(12) United States Patent
Nakai et al.

(10) Patent No.: US 11,993,697 B2
(45) Date of Patent: May 28, 2024

(54) FLEXIBLE TUBE FOR ENDOSCOPE, ENDOSCOPIC MEDICAL DEVICE, AND RESIN COMPOSITION FOR COVERING FLEXIBLE TUBE SUBSTRATE FOR ENDOSCOPE

(71) Applicant: FUJIFILM Corporation, Tokyo (JP)

(72) Inventors: Yoshihiro Nakai, Ashigarakami-gun (JP); Kazushi Furukawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 925 days.

(21) Appl. No.: 17/022,662

(22) Filed: Sep. 16, 2020

(65) Prior Publication Data

US 2020/0405918 A1  Dec. 31, 2020

Related U.S. Application Data

(63) Continuation of application No. PCT/JP2019/012609, filed on Mar. 25, 2019.

(30) Foreign Application Priority Data

Mar. 28, 2018 (JP) ................................. 2018-063153

(51) Int. Cl.
*C08K 5/32* (2006.01)
*A61B 1/005* (2006.01)
(Continued)

(52) U.S. Cl.
CPC ................ *C08K 5/32* (2013.01); *A61B 1/005* (2013.01); *A61L 29/06* (2013.01); *A61L 29/085* (2013.01);
(Continued)

(58) Field of Classification Search
CPC .......... C08K 5/32; C08K 5/13; C08K 5/3435; C08K 5/372; C08K 5/524; A61B 1/005;
(Continued)

(56) References Cited

U.S. PATENT DOCUMENTS

2007/0238835 A1   10/2007  Chen
2011/0028621 A1*   2/2011  Martens .................. C08L 77/00
                                                                524/323

(Continued)

FOREIGN PATENT DOCUMENTS

CN        105074306 A      11/2015
CN        105455764 A       4/2016
(Continued)

OTHER PUBLICATIONS

Communication dated Apr. 23, 2021, from the European Patent Office in European Application No. 19777274.2.
(Continued)

*Primary Examiner* — James C Yager
(74) *Attorney, Agent, or Firm* — Sughrue Mion, PLLC

(57) ABSTRACT

A flexible tube for an endoscope has a flexible tube substrate that is flexible and tubular and a resin layer (A) covering the flexible tube substrate. The resin layer (A) includes a thermoplastic resin (a) including at least one of a polyamide resin, a polyurethane resin, a polyester resin, a polystyrene resin, or an acrylic resin and having a tensile strength at 10% elongation of 10 MPa or more and a hindered amine compound (b) having a molecular weight of 500 or more. Also provided are an endoscopic medical device including the flexible tube for an endoscope and a resin composition suitable for forming the resin layer of the flexible tube for an endoscope.

15 Claims, 2 Drawing Sheets

(51) Int. Cl.
| | |
|---|---|
| *A61L 29/06* | (2006.01) |
| *A61L 29/08* | (2006.01) |
| *A61L 29/14* | (2006.01) |
| *C08K 5/13* | (2006.01) |
| *C08K 5/3435* | (2006.01) |
| *C08K 5/372* | (2006.01) |
| *C08K 5/524* | (2006.01) |
| *A61M 25/00* | (2006.01) |

(52) U.S. Cl.
CPC ............... *A61L 29/14* (2013.01); *C08K 5/13* (2013.01); *C08K 5/3435* (2013.01); *C08K 5/372* (2013.01); *C08K 5/524* (2013.01); *A61M 25/005* (2013.01); *A61M 2025/0059* (2013.01)

(58) Field of Classification Search
CPC ...... A61B 1/0011; A61L 29/06; A61L 29/085; A61L 29/14; A61L 29/143; A61M 25/005; A61M 2025/0059; A61M 25/0043; A61M 25/0052; C08L 101/12; C08L 77/00; C08L 75/04; C08L 67/02; C08L 33/08; C09D 177/02; C09D 177/06; C08G 69/40; B32B 2250/02; B32B 2307/54; B32B 2307/546; B32B 27/40; B32B 2307/536; B32B 2307/702; B32B 2307/714; B32B 2535/00; B32B 1/08; B32B 15/082; B32B 15/088; B32B 15/09; B32B 15/095; B32B 15/18; B32B 27/18; B32B 28/302; B32B 27/308; B32B 27/34; B32B 27/36

See application file for complete search history.

(56) References Cited

U.S. PATENT DOCUMENTS

| | | |
|---|---|---|
| 2015/0202352 A1 | 7/2015 | Watanabe |
| 2016/0024343 A1 | 1/2016 | Nakai et al. |
| 2016/0088998 A1 | 3/2016 | Nagai et al. |
| 2020/0100646 A1 | 4/2020 | Furukawa et al. |
| 2020/0107697 A1 | 4/2020 | Furukawa et al. |

FOREIGN PATENT DOCUMENTS

| | | |
|---|---|---|
| CN | 110709000 A | 1/2020 |
| CN | 110769735 A | 2/2020 |
| EP | 2 896 635 A1 | 7/2015 |
| EP | 2 980 466 A1 | 2/2016 |
| EP | 3 646 770 A1 | 5/2020 |
| EP | 3 646 900 A1 | 5/2020 |
| JP | 2015-16261 A | 1/2015 |
| JP | 2015-154924 A | 8/2015 |
| JP | 2015-200352 A | 11/2015 |

OTHER PUBLICATIONS

International Search Report dated Jun. 11, 2019 from the International Searching Authority in International Application No. PCT/JP2019/012609.
Written Opinion dated Jun. 11, 2019 from the International Bureau in International Application No. PCT/JP2019/012609.
International Preliminary Report on Patentability dated Sep. 29, 2020 with translation of the Written Opinion from the International Bureau in International Application No. PCT/JP2019/012609.
Communication dated Oct. 21, 2023, issued in Chinese Application No. 201980019439.X.

\* cited by examiner

FLEXIBLE TUBE FOR ENDOSCOPE, ENDOSCOPIC MEDICAL DEVICE, AND RESIN COMPOSITION FOR COVERING FLEXIBLE TUBE SUBSTRATE FOR ENDOSCOPE

CROSS-REFERENCE TO RELATED APPLICATIONS

This application is a Continuation of PCT International Application No. PCT/JP2019/012609 filed on Mar. 25, 2019, which claims priority under 35 U.S.C. § 119 (a) to Japanese Patent Application No. 2018-063153 filed in Japan on Mar. 28, 2018. Each of the above applications is hereby expressly incorporated by reference, in its entirety, into the present application.

BACKGROUND OF THE INVENTION

1. Field of the Invention

The present invention relates to flexible tubes for endoscopes, endoscopic medical devices, and resin compositions for covering flexible tube substrates for endoscopes.

2. Description of the Related Art

Endoscopes are medical devices for examination of a patient's body cavity. Since an endoscope is inserted and used in a body cavity, an endoscope that does not damage an organ or cause pain and/or discomfort to a patient is desirable. To meet this need, a spiral tube formed by spirally winding a flexible metal strip is used as a flexible tube that forms the insertion section of an endoscope. In addition, the periphery of the spiral tube is covered with a flexible resin so that the spiral tube does not cause stimulation or damage to the surface of a body cavity such as the esophagus or intestine.

Endoscopes for examination of a human body cavity are repeatedly used. Therefore, the flexible tube that forms the insertion section of an endoscope needs to be cleaned and disinfected with a chemical after each use. Accordingly, there is a need for an endoscope having the property of not being degraded after repeated disinfection. For example, JP2015-16261A discloses that a resin layer covering a flexible tube substrate contains a polyester elastomer and a hindered phenol compound or hindered amine compound to improve the durability to disinfection with peracetic acid and aqueous hydrogen peroxide.

SUMMARY OF THE INVENTION

The requirements on the sterilization durability, handleability, and other properties of flexible tubes for endoscopes are becoming more stringent year by year. For example, to prevent infectious diseases, there is a need for a high level of cleanliness sufficient not only for disinfection, but also for sterilization, particularly for insertion into a site where there is a high risk of infection, such as a bronchus. Accordingly, it has been desirable to apply a treatment with higher sterilizing power. In addition, endoscopic procedures such as for examination and medical treatment have also been applied to thin cavities such as bronchi, and there is a need for an endoscope having a thinner insertion section with a thinner flexible tube substrate.

In addition, to smoothly and reliably deliver such a thin endoscope insertion section to an affected area or other site to obtain its detailed information and to accurately treat the affected area with the endoscope, there is a need for a flexible tube substrate that not only has flexibility, but also has certain rigidity (desired bending hardness) sufficient to resist buckling, for example, when sharply bent.

Furthermore, there is a need for an endoscope insertion section having the property of resisting peeling between a flexible tube substrate and a resin layer covering the flexible tube substrate when repeatedly bent (bending durability).

In view of the foregoing, an object of the present invention is to provide a flexible tube for an endoscope with the desired bending hardness, superior bending durability, and high sterilization durability, an endoscopic medical device including such a flexible tube for an endoscope, and a resin composition with good molding stability that is suitable for forming a resin layer of such a flexible tube for an endoscope.

After conducting intensive research in view of the foregoing problems, the inventors have found that the foregoing problems can be solved by the use of a particular thermoplastic resin having a tensile strength at 10% elongation of 10 MPa or more and a hindered amine compound having a particular molecular weight or more as constituent materials for a resin layer of a flexible tube for an endoscope, thus completing the present invention.

The foregoing object is achieved by the following solutions:

(1) A flexible tube for an endoscope has a flexible tube substrate that is flexible and tubular and a resin layer (A) covering the flexible tube substrate. The resin layer (A) includes a thermoplastic resin (a) including at least one of a polyamide resin, a polyurethane resin, a polyester resin, a polystyrene resin, or an acrylic resin and having a tensile strength at 10% elongation of 10 MPa or more and a hindered amine compound (b) having a molecular weight of 500 or more.

(2) In the flexible tube for an endoscope according to (1), the thermoplastic resin (a) has a tensile strength at 10% elongation of 10 MPa to 50 MPa.

(3) In the flexible tube for an endoscope according to (1) or (2), the polyamide resin includes at least one of polyamide 1010, polyamide 1012, polyamide 11, polyamide 12, a polyamide elastomer, or an amorphous polyamide.

(4) In the flexible tube for an endoscope according to (3), the polyamide resin includes at least one of polyamide 11, polyamide 12, or a polyamide elastomer.

(5) In the flexible tube for an endoscope according to any one of (1) to (4), the polyurethane resin has an aliphatic diisocyanate-derived component.

(6) In the flexible tube for an endoscope according to any one of (1) to (5), the polyurethane resin has a poly(alkyleneoxy) structure in which the alkylene has 6 or more carbon atoms.

(7) In the flexible tube for an endoscope according to any one of (1) to (6), the polyester resin has a polybutylene naphthalate structure.

(8) In the flexible tube for an endoscope according to any one of (1) to (7), the acrylic resin has two or more acrylic acid ester components, each acrylic acid ester component forming a block structure.

(9) In the flexible tube for an endoscope according to any one of (1) to (8), the hindered amine compound (b) has a molecular weight of 1,000 or more.

(10) In the flexible tube for an endoscope according to any one of (1) to (9), the hindered amine compound (b)

includes at least one of an N—R type hindered amine compound or an N—OR type hindered amine compound.

(11) In the flexible tube for an endoscope according to any one of (1) to (10), the amount of the hindered amine compound (b) is 0.2% to 8% by mass based on 100% by mass of all components forming the resin layer (A).

(12) In the flexible tube for an endoscope according to any one of (1) to (11), the resin layer (A) includes an antioxidant (c).

(13) In the flexible tube for an endoscope according to (12), the antioxidant (c) includes at least one of a phosphite-based antioxidant or a thioether-based antioxidant.

(14) In the flexible tube for an endoscope according to (12) or (13), the amount of the antioxidant (c) in the resin layer (A) is 0.15% to 4% by mass.

(15) An endoscopic medical device includes the flexible tube for an endoscope according to any one of (1) to (14).

(16) A resin composition for covering a flexible tube substrate for an endoscope includes a thermoplastic resin (a) including at least one of a polyamide resin, a polyurethane resin, a polyester resin, a polystyrene resin, or an acrylic resin and having a tensile strength at 10% elongation of 10 MPa or more; and a hindered amine compound (b) having a molecular weight of 500 or more.

In the description of the present invention, if there are a plurality of substituents, linking groups, or the like (hereinafter referred to as "substituents or the like") represented by a particular symbol, or if a plurality of substituents or the like are specified simultaneously or alternatively, it is meant that the individual substituents or the like may be the same or different. In addition, if a plurality of substituents or the like are adjacent to each other, it is meant that they may be linked or fused to each other to form a ring, even if not specified as such.

In the description of the present invention, if it is not explicitly specified whether a substituent (or linking group) is substituted or unsubstituted, it is meant that the group may have any substituent as long as the desired effect is achieved. This also applies if it is not explicitly specified whether a compound is substituted or unsubstituted.

In the description of the present invention, the term "acrylic" refers to a wide range of structures having an acryloyl group, including those having a substituent (e.g., an alkyl group (preferably, a methyl group)) at the α position.

The flexible tube for an endoscope according to the present invention can achieve the desired bending hardness, superior bending durability, and high sterilization durability. The endoscopic medical device according to the present invention includes the flexible tube for an endoscope with the above superior properties. The resin composition for covering a flexible tube substrate for an endoscope according to the present invention is suitable for use as a constituent material for the resin layer of the flexible tube for an endoscope with the above properties.

DESCRIPTION OF THE PREFERRED EMBODIMENTS

Figure 1:
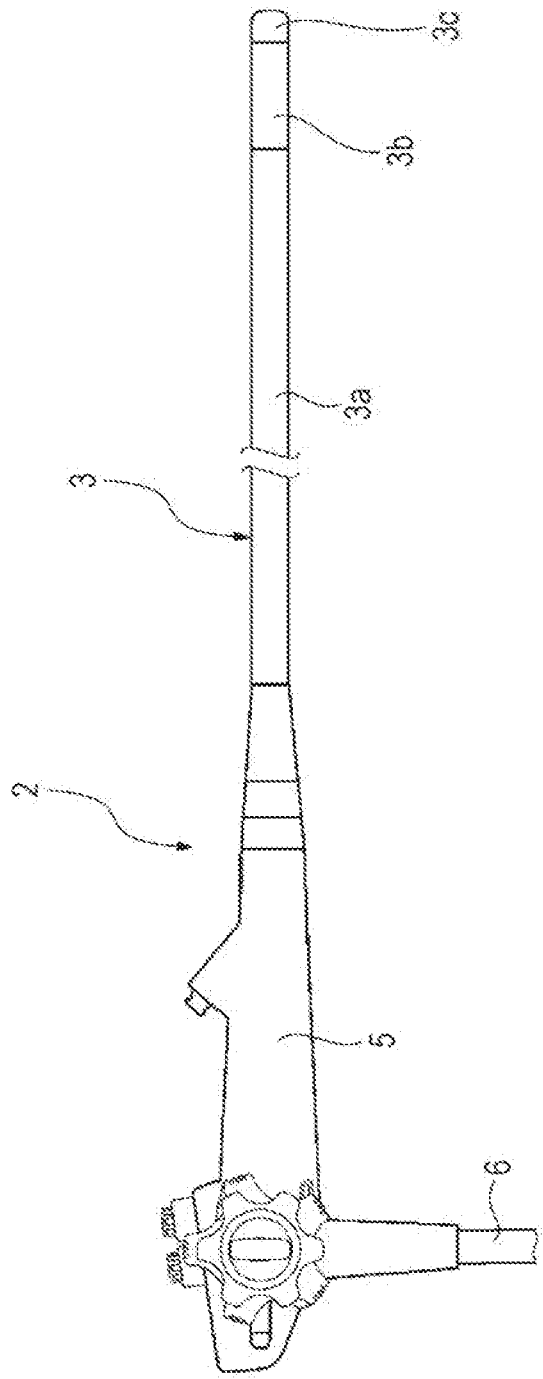
FIG. 1 is an external view illustrating the configuration of an electronic endoscope.

An electronic endoscope will now be described as an example of an endoscopic medical device according to a preferred embodiment of the present invention. Electronic endoscopes incorporate a flexible tube for an endoscope (a flexible tube for an endoscope may be hereinafter simply referred to as "flexible tube") and are widely used as medical devices. In an example shown in FIG. 1, an electronic endoscope 2 includes an insertion section 3 for insertion into a body cavity, a main-body operating section 5 connected to the proximal end portion of the insertion section 3, and a universal cord 6 for connection to a processor device and a light source device. The insertion section 3 is composed of a flexible tube 3a connected to the main-body operating section 5, an angle portion 3b connected to the flexible tube 3a, and a tip portion 3c connected to the distal end of the angle portion 3b and having an imaging device (not shown) built thereinto for imaging a body cavity. The flexible tube 3a, which accounts for most of the length of the insertion section 3, is flexible substantially over the entire length thereof. In particular, the portion to be inserted into a site such as a body cavity has a more flexible structure.

Flexible Tube

Figure 2:
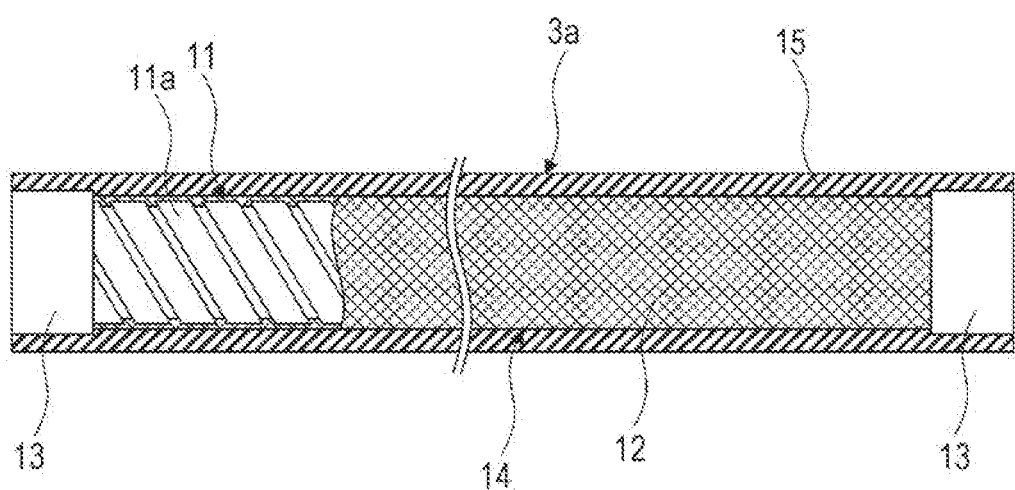
FIG. 2 is a partial sectional view schematically illustrating the configuration of a flexible tube for an endoscope.

As shown in FIG. 2, the flexible tube 3a (flexible tube for an endoscope) has a flexible tube substrate 14 and a resin layer 15 (resin layer (A)) covering the outer peripheral surface of the flexible tube substrate 14. The flexible tube substrate 14 includes a spiral tube 11 disposed on the innermost side and formed by spirally winding a metal strip 11a, a tubular net 12 covering the spiral tube 11 and formed by weaving metal wires, and caps 13 fitted to both ends. Although the spiral tube 11 is shown as a single layer, it may be composed of two layers coaxially stacked on top of each other. To clearly illustrate the layer structure, the resin layer 15 is shown as being thick relative to the diameter of the flexible tube substrate 14.

In this embodiment, the resin layer 15 is formed with substantially uniform thickness in the longitudinal direction (axial direction) of the flexible tube substrate 14. The resin layer 15 has a thickness of, for example, 0.1 to 0.6 mm. The flexible tube 3a has an outer diameter D of, for example, 2.0 to 10.0 mm, preferably 3.0 to 8.0 mm. In addition, the flexible tube substrate 14 has an outer diameter of, for example, 1.6 to 9.6 mm, preferably 2.2 to 7.8 mm.

Method for Manufacturing Flexible Tube for Endoscope

The flexible tube for an endoscope according to the present invention can be manufactured as usual except for the configuration of the resin layer (A). For example, the flexible tube for an endoscope according to the present invention can be manufactured by referring to JP2014-188217A, JP2015-16261A, and JP2016-209659A.

The flexible tube according to the present invention has a flexible tube substrate that is flexible and tubular and a resin layer (A) covering the flexible tube substrate. The resin layer (A) includes a thermoplastic resin (a) (resin component, component (a)) having a tensile strength at 10% elongation of 10 MPa or more and a hindered amine compound (b) (component (b)) having a molecular weight of 500 or more. The thermoplastic resin (a) includes at least one of a polyamide resin, a polyurethane resin, a polyester resin, a polystyrene resin, or an acrylic resin.

The resin layer (A) may be composed of a single layer or a plurality of layers with different compositions. In addition, the flexible tube according to the present invention may have, outside the resin layer (A), for example, a topcoat layer described in JP2015-16261A.

With the above configuration of the resin layer (A), the flexible tube according to the present invention has both flexibility and certain rigidity required of an endoscope insertion section and can also achieve a higher adhesiveness to the flexible tube substrate (bending durability) and the desired sufficient chemical resistance. Although the mechanism is not fully understood, one possible explanation is as follows. Because the resin layer (A) contains, as a matrix, a thermoplastic resin having a tensile strength at 10% elongation of 10 MPa or more and having a particular bond or benzene ring and further contains a hindered amine compound (b) having a particular molecular weight or more, a certain stress is induced in the resin layer (A) at the interface with the flexible tube substrate upon bending. When the flexible tube is repeatedly bent in various directions, the certain stress induced in the resin layer (A) allows it to return to its original form (unbent state) while highly maintaining its adhesiveness to the flexible tube substrate. Furthermore, because the resin layer (A) has superior shape stability, the migration of the hindered amine compound (b) from the resin layer (A) is highly inhibited.

Thermoplastic Resin (a)

The thermoplastic resin (a) may be any thermoplastic resin that includes at least one of a polyamide resin, a polyurethane resin, a polyester resin, a polystyrene resin, or an acrylic resin and that has a tensile strength at 10% elongation of 10 MPa or more. The tensile strength at 10% elongation of the thermoplastic resin (a) is calculated by the method described in the Examples section later.

The total amount of the polyamide resin, the polyurethane resin, the polyester resin, the polystyrene resin, and the acrylic resin present in the thermoplastic resin (a) is preferably 70% by mass or more, more preferably 90% by mass or more, and may be 100% by mass. Examples of thermoplastic resins other than polyamide resins, polyurethane resins, polyester resins, polystyrene resins, and acrylic resins that can be present in the thermoplastic resin (a) include polycarbonate resins, polyacetal resins, and polyphenylene ether resins.

The total amount of the thermoplastic resin (a) in the resin component forming the resin layer (A) is preferably 70% by mass or more, more preferably 90% by mass or more, even more preferably 96% by mass or more, and may be 100% by mass. Examples of resins and polymers other than the thermoplastic resin (a) that can be present in the resin layer (A) include polyvinyl chloride resins.

In the present invention, the tensile strength at 10% elongation is preferably 10 MPa to 50 MPa, more preferably 15 MPa to 45 MPa, particularly preferably 20 MPa to 40 MPa. If the tensile strength at 10% elongation falls within the above range, the stress induced at the interface between the resin layer (A) and the flexible tube substrate decreases, thus inhibiting peeling at the interface and further improving the bending durability.

To further improve the bending durability, the thermoplastic resin (a) preferably has a surface hardness of 45 D to 85 D, more preferably 50 D to 80 D, particularly preferably 60 D to 75 D. The surface hardness is calculated by the method described in the Examples section later.

Polyamide Resin

Examples of polyamide resins include crystalline polyamides, amorphous polyamides, and polyamide elastomers having tensile strengths at 10% elongation of 10 MPa or more.

Examples of crystalline polyamides include aliphatic polyamides and aromatic polyamides.

Examples of aliphatic polyamides include poly-ε-capramide (polyamide 6), polytetramethylene adipamide (polyamide 46), polyhexamethylene adipamide (polyamide 66), polycapramide/polyhexamethylene adipamide copolymer (polyamide 6/66), polyundecamide (polyamide 11), polycapramide/polyundecamide copolymer (polyamide 6/11), polydodecamide (polyamide 12), polycapramide/polydodecamide copolymer (polyamide 6/12), polyhexamethylene sebacamide (polyamide 610), polydecamethylene sebacamide (polyamide 1010), polyhexamethylene dodecamide (polyamide 612), polydecamethylene dodecamide (polyamide 1012), polyundecamethylene adipamide (polyamide 116), and mixtures and copolymers thereof.

Examples of aromatic polyamides include polyhexamethylene isophthalamide (polyamide 6I), polyhexamethylene terephthalamide (polyamide 6T), polyhexamethylene terephthalamide/polyhexamethylene isophthalamide copolymer (polyamide 6T/6I), polycapramide/polyhexamethylene terephthalamide copolymer (polyamide 6/6T), polycapramide/polyhexamethylene isophthalamide copolymer (polyamide 6/6I), polyhexamethylene adipamide/polyhexamethylene terephthalamide copolymer (polyamide 66/6T), polyhexamethylene adipamide/polyhexamethylene isophthalamide copolymer (polyamide 66/6I), polytrimethythexamethylene terephthalamide (polyamide TMDT), polybis(4-aminocyclohexyl)methane dodecamide (polyamide PACM 12), polybis(3-methyl-4-aminocyclohexyl)methane dodecamide (nylon dimethyl PACM 12), poly-m-xylylene adipamide (polyamide MXD6), polydecamethylene terephthalamide (polyamide 10T), polyundecamethylene terephthalamide (polyamide 11T), and mixtures and copolymers thereof.

Examples of amorphous polyamides include isophthalic acid/terephthalic acid/1,6-hexanediamine/bis(3-methyl-4-aminocyclohexyl)methane polycondensate, terephthalic acid/2,2,4-trimethyl-1,6-hexanediamine/2,4,4-trimethyl-1,6-hexabediamine polycondensate, isophthalic acid/bis(3-methyl-4-aminocyclohexyl)methane/ω-laurolactam polycondensate, isophthalic acid/terephthalic acid/1,6-hexanediamine polycondensate, isophthalic acid/2,2,4-trimethyl-1,6-hexanediamine/2,4,4-trimethyl-1,6-hexandiamine polycondensate, isophthalic acid/terephthalic acid/2,2,4-trimethyl-1,6-hexanediamine/2,4,4-trimethyl-1,6-hexanediamine polycondensate, isophthalic acid/bis(3-methyl-4-aminocyclohexyl)methane/ω-laurolactam polycondensate, and isophthalic acid/terephthalic acid polycondensates with other diamine components.

Examples of polyamide elastomers include multiblock copolymers containing polyamide hard segments and polyether or polyester soft segments. Examples of hard segments include polyamide 6, polyamide 66, polyamide 610, polyamide 11, and polyamide 12. Examples of polyethers for soft segments include polyethylene glycol, poly(oxytetramethylene) glycol, and poly(oxypropylene) glycol. Examples of polyesters include poly(ethylene adipate) glycol and poly(butylene-L4-adipate)

Preferred polyamides for use in the present invention include polyamide 1010, polyamide 1012, polyamide 11, polyamide 12, polyamide elastomers, and amorphous polyamides. To further improve the bending hardness, the bending durability, and the sterilization durability, polyamide 11, polyamide 12, and polyamide elastomers are preferred.

Examples of commercially available polyamide resins for use in the present invention include polyamide 11 (the trade name "Rilsan BMIN O" available from Arkema Inc.), polyamide 12 (the trade name "Vestamid L1940" available from Daicel-Evonik Ltd.), polyamide 1010 (the trade name "Vestamid Terra DS16" available from Daicel-Evonik Ltd.), polyamide 1012 (the trade name "Vestamid Terra DD16" available from Evonik), amorphous polyamides (the trade name "Trogamid CX7323" available from Daicel-Evonik Ltd.), and polyamide elastomers (the trade name "Pebax 7233" and "Pebax Rnew 80R53" available from Arkema Inc.).

Polyurethane Resin

Examples of polyurethane resins that can be used include carbonate-based, ether-based, and ester-based polyurethane resins having tensile strengths at 10% elongation of 10 MPa or more. Polyurethane elastomers are also preferred. Suitable polyurethane elastomers can be selected depending on the purpose. Examples of polyurethane elastomers include elastomers including structural units of hard segments formed from a low-molecular-weight glycol and a diisocyanate and soft segments formed from a polymeric (long-chain) diol and a diisocyanate.

Diisocyanates may be either aliphatic diisocyanates or aromatic diisocyanates. Specific examples of aliphatic diisocyanates include hexamethylene diisocyanate and dicyclohexylmethane 4,4'-diisocyanate. Specific examples of aromatic diisocyanates include m-xylylene diisocyanate and 4,4'-diphenylmethane diisocyanate.

Examples of polymeric (long-chain) diols include polyalkylene glycols, poly(1,4-butylene adipate), poly(ethylene/1,4-butylene adipate), polycaprolactone, poly(1,6-hexylene carbonate), and poly(1,6-hexylene/neopentylene adipate). Polymeric (long-chain) diols preferably have a number average molecular weight of 500 to 10,000.

Examples of low-molecular-weight glycols that can be used include short-chain diols such as ethylene glycol, propylene glycol, 1,4-butanediol, and bisphenol A. Short-chain diols preferably have a number average molecular weight of 48 to 500.

To further improve the bending durability, the polyurethane used in the present invention preferably has an aliphatic diisocyanate-derived component in its repeating units. In addition, to further improve the bending durability and the sterilization durability, the polyurethane used in the present invention preferably has repeating units having a polyalkylene glycol-derived component. The alkylene in the polyalkylene glycol-derived component preferably contains 2 or more carbon atoms, more preferably 4 or more carbon atoms, particularly preferably 6 or more carbon atoms. The upper limit is preferably 12 or less carbon atoms, more preferably 10 or less carbon atoms.

Examples of commercially available polyurethane resins for use in the present invention include aliphatic ether-based polyurethanes (the trade name "Tecoflex EG-72D" available from Lubrizol Corporation), aliphatic carbonate-based polyurethanes (the trade name "Carbothane PC-3572D" available from Lubrizol Corporation), aromatic ether-based polyurethanes (the trade name "Miractran E574PNAT" available from Nippon Polyurethane Industry Co., Ltd.), and aromatic other-based polyurethanes (the trade name "Isoplast 2510" available from Lubrizol Corporation).

Polyester Resin

Examples of polyester resins include polyester resins composed of a dicarboxylic acid component and a diol component and having tensile strengths at 10% elongation of 10 MPa or more and polyester resins composed of a hydroxycarboxylic acid component and having tensile strengths at 10% elongation of 10 MPa or more.

Examples of dicarboxylic acid components include terephthalic acid, isophthalic acid, phthalic acid, 2,6-naphthalenedicarboxylic acid, 5-sodiosulfoisophthalic acid, oxalic acid, succinic acid, adipic acid, sebacic acid, azelaic acid, dodecanedioic acid, dimer acids, maleic anhydride, maleic acid, fumaric acid, itaconic acid, citraconic acid, mesaconic acid, and cyclohexanedicarboxylic acid.

Examples of diol components include ethylene glycol, diethylene glycol, 1,3-propanediol, 1,4-butanediol, neopentyl glycol, 1,6-hexanediol, cyclohexanedimethanol, triethylene glycol, polyethylene glycol, polypropylene glycol, polytetramethylene glycol, and ethylene oxide adducts of bisphenol A and bisphenol S.

Examples of hydroxycarboxylic acid components include α-caprolactone, lactic acid, and 4-hydroxybenzoic acid.

The polyester resin may be a homopolymer of any of the above components or a copolymer thereof and may contain a small amount of a trifunctional compound component such as trimellitic acid, trimeric acid, pyromellitic acid, trimethylolpropane, glycerol, or pentaerythritol.

As the polyester resin, two or more of such homopolymers and copolymers of the above components may be used in combination.

It is also preferred that the polyester resin be a polyester elastomer. For example, block copolymers composed of high-melting-point polyester segments (hard segments) and low-melting-point polymer segments (soft segments) having a molecular weight of 400 to 6,000 can be used, for example, as described in JP1999-92636A (JP-H11-92636A).

To further improve the bending durability, the polyester resin used in the present invention preferably has a polybutylene naphthalate-derived structure.

Examples of commercially available polyester resins for use in the present invention include polyester elastomers (the trade name "Hytrel 5557" and "Hytrel 7247" available from DuPont-Toray Co., Ltd.) and polyester elastomers (the trade name "TQB-KET 30" available from Teijin Limited).

Polystyrene Resin

The polystyrene resin refers to a resin including 50% by mass or more of a styrene component and having a tensile strength at 10% elongation of 10 MPa or more. The styrene component is a structural unit derived from a monomer having a styrene skeleton in its structure.

Examples of polystyrene resins include homopolymers of styrene compounds and copolymers of two or more styrene compounds. As used herein, "styrene compound" refers to a compound having a styrene skeleton in its structure and is meant to include styrene and compounds derived from styrene by introducing a substituent into a site other than the ethylenically unsaturated bond. Examples of styrene compounds include styrene; alkylstyrenes such as α-methylstyrene, o-methylstyrene, m-methylstyrene, p-methylstyrene, 1,3-dimethylstyrene, 2,4-dimethylstyrene, o-ethylstyrene, p-ethylstyrene, and tert-butylstyrene; and substituted styrenes derived from styrene by introducing a substituent such as a hydroxy group, an alkoxy group, a carboxyl group, or a halogen into the benzene core, including hydroxystyrene, tert-butoxystyrene, vinylbenzoic acid, o-chlorostyrene, and p-chlorostyrene.

The polystyrene may include any constituent component other than the styrene component. Specifically, the polystyrene resin may be a styrene-diene copolymer or a styrene-polymerizable unsaturated carboxylic acid ester copolymer. Mixtures of polystyrene with synthetic rubbers (e.g., polybutadiene and polyisoprene) can also be used. So-called styrene-based elastomers are also suitable for use.

The polystyrene resin may be hydrogenated (may be a hydrogenated polystyrene) Preferred hydrogenated polystyrenes include, but not limited to, hydrogenated styrenediene-based copolymers such as hydrogenated styrene-butadiene-styrene block copolymer (SEBS) and hydrogenated styrene-isoprene-styrene block copolymer (SEPS), which are resins obtained by hydrogenation of SBS and SIS, respectively. These hydrogenated polystyrene resins may be used alone or in combination.

Examples of commercially available styrene resins for use in the present invention include styrene-based elastomers (the trade name "Septan 2104" available from Kuraray Co., Ltd.).

Acrylic Resin

Examples of acrylic resins include polymers and elastomers obtained by polymerization of a starting monomer containing an acrylic acid ester as a main component and having tensile strengths at 10% elongation of 10 MPa or more. Examples of acrylic acid esters include methyl methacrylate, methyl acrylate, ethyl methacrylate, ethyl acrylate, butyl acrylate, methoxyethyl acrylate, and ethoxyethyl acrylate. Acrylic resins obtained using a starting material such as glycidyl methacrylate or allyl glycidyl ether as a crosslink monomer can also be used. In addition, these acrylic resins may optionally be copolymerized with, for example, acrylic acid or methacrylic acid.

Furthermore, these acrylic resins may be copolymerized with, for example, acrylonitrile. Specific examples include acrylonitrile-butyl acrylate copolymer, acrylonitrile-butyl acrylate-ethyl acrylate copolymer, and acrylonitrile-butyl acrylate glycidyl methacrylate copolymer.

To achieve moderate flexibility and hardness for use as a flexible tube for an endoscope, the acrylic resin used in the present invention is preferably a copolymer having two or more acrylic acid ester components, each acrylic acid ester component forming a block structure. Preferred examples include acrylic resins having a methyl methacrylate block-methyl acrylate block-methyl methacrylate block structure and acrylic resins having a methyl acrylate block-methyl methacrylate block structure.

Examples of commercially available acrylic resins for use in the present invention include acrylic-based elastomers (the trade name "Kurarity LM730H" available from Kuraray Co., Ltd.).

Hindered Amine Compound (b)

The hindered amine compound (b) used in the present invention is a normal hindered amine light stabilizer (HALS) having a molecular weight of 500 or more.

The hindered amine compound (b) is preferably a compound having a structural moiety represented by general formula (3) below.

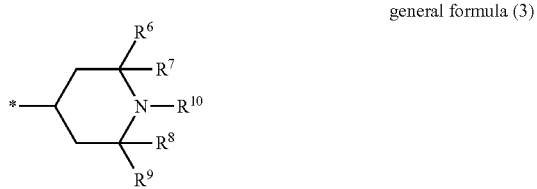

general formula (3)

In general formula (3), $R^6$ to $R^9$ represent a hydrogen atom or an alkyl group having 1 to 12 carbon atoms (preferably 1 to 8 carbon atoms, more preferably 1 to 5 carbon atoms). Specific examples of alkyl groups represented by $R^6$ to $R^9$ include methyl, ethyl, n-butyl, isopropyl, s-butyl, t-butyl, t-pentyl, t-hexyl, and t-octyl. Preferably, $R^6$ to $R^9$ are primary (linear) alkyl groups. More preferably, all of $R^6$ to $R^9$ are primary (linear) alkyl groups (particularly preferably methyl groups).

In general formula (3), $R^{10}$ represents a hydrogen atom, an alkyl group having 1 to 18 carbon atoms (preferably 1 to 10 carbon atoms, more preferably 1 to 5 carbon atoms, even more preferably 1 to 3 carbon atoms, further preferably 1 or 2 carbon atoms), or $—OR^{11}$, where represents a hydrogen atom or a linear, branched, or cyclic alkyl group having 1 to 20 carbon atoms (preferably 1 to 12 carbon atoms). In particular, $R^{10}$ is preferably an alkyl group or an alkoxy group, which results in a higher sterilization durability If the hindered amine compound (b) is a polymer, $R^{10}$ in general formula (3) may be a simple direct bond (—) or a divalent linking group. If $R^{10}$ is a divalent linking group, an alkylene group (preferably having 1 to 12 carbon atoms, more preferably 1 to 8 carbon atoms, even more preferably 1 to 5 carbon atoms) is preferred.

In general formula (3), * represents a point of attachment.

The component (b) has a molecular weight of 500 or more, preferably 650 or more, more preferably 800 or more, even more preferably 1,000 or more. Although there is no particular upper limit, the component (b) preferably has a molecular weight of 10,000 or less, more preferably 5,000 or less. The desorption of the component (b) from the surface of the resin layer (A) can be reduced, and the degradation of the resin component due to sterilization treatment can be more effectively reduced, thus further improving the sterilization durability.

If the component (b) has a molecular weight distribution, the above molecular weight refers to the number average molecular weight. The number average molecular weight is calculated by the following measurement method.

An HLC-8220 (trade name, available from Tosoh Corporation) GPC apparatus is used. The eluant used is tetrahydrofuran. The columns used are G3000XHL and G2000HXL (both of which are trade names, available from Tosoh Corporation). The temperature is 23° C. The flow rate is 1 mL/min. An RI detector can be used for detection.

The component (b) may be an N—H type hindered amine compound, an N—R type hindered amine compound, or an N—OR type hindered amine compound. In the present invention, it is preferred to use an N—R type hindered amine compound or an N—OR type hindered amine compound. This is because the degradation of the resin component due to sterilization treatment can be more effectively reduced, thus further improving the sterilization durability.

N—H type hindered amine compounds have a hydrogen atom attached to a nitrogen atom in a piperidine skeleton. Specific examples of N—H type hindered amine light stabilizers include Tinuvin 770 DF, Chimassorb 2020 FDL, and Chimassorb 944 FDL (all of which are trade names, available from BASF); ADK STAB LA-68 and ADK STAB LA-57 (both of which are trade names, available from Adeka Corporation); and Cyasorb UV-3346 and Cyasorb UV-3853 (both of which are trade names, available from Sun Chemical Company Ltd.).

N—R type hindered amine compounds have an organic group R (R is an alkyl group represented by $R^{10}$ above) attached to a nitrogen atom in a piperidine skeleton. Specific examples of N—R type hindered amine compounds include Tinuvin 622 SF. Tinuvin 765, Tinuvin PA 144, Chimassorb 119, and Tinuvin 111 (all of which are trade names, available from BASF); Sabostab UV 119 (trade name, available from Sabo S.p.A.); and ADK STAB LA-63P and ADK STAB LA-52 (both of which are trade names, available from Adeka Corporation).

N—OR type hindered amine compounds have —OR (R is an alkyl group represented by $R^{11}$ above) attached to a nitrogen atom in a piperidine skeleton. Specific examples of N—OR type hindered amine compounds include Tinuvin 123, Tinuvin 5100, Tinuvin NOR 371 FF, and Flamestab NOR 116 FF (all of which are trade names, available from BASF).

These components (h) may be used alone or in combination.

In the present invention, the amount of the component (b) is preferably 0.2% to 8% by mass, more preferably 0.2% to 4% by mass, based on 100% by mass of all components forming the resin layer (A). If the amount of the component (b) is not less than the above lower limit, the sterilization durability can be further improved. On the other hand, if the amount of the component (b) is not more than the above upper limit, the bending hardness and the bending durability can be further improved.

Antioxidant (c)

In the present invention, the resin layer (A) preferably includes an antioxidant (c) to further improve the bending durability. Various antioxidants can be used as the component (c), including phenol-based antioxidants, amine-based antioxidants, phosphorus-based (phosphite-based) antioxidants, sulfur-based (thioether-based) antioxidants, hydrazine-based antioxidants, and amide-based antioxidants.

In the present invention, a phosphite-based antioxidant or a thioether-based antioxidant is preferably used as the component (c) to further improve the bending durability.

Phosphite-Based Antioxidant

The phosphite-based antioxidant is preferably a compound having a structure represented by general formula (I):

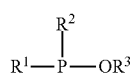

general formula (1)

In general formula (1), $R^1$ and $R^2$ represent an alkyl group, an aryl group, an alkoxy group, an aryloxy group, or a halogen atom; $R^3$ represents an alkyl group or an aryl group; and at least two of $R^1$, $R^2$, or $R^3$ may be linked to each other via a divalent or higher-valent group or a single bond.

In the present invention, compounds having a structure represented by general formula (1) include, in addition to compounds represented by general formula (1), compounds (i) and (ii) below.

(i) Compounds having a structure in which a monovalent group derived by removing one hydrogen atom from $R^1$, $R^2$, or $R^3$ is linked to at least one of $R^1$, $R^2$, or $R^3$ of one or more (preferably one to three) other compounds represented by general formula (1) via a divalent or higher-valent group or a single bond; and (ii) compounds having a structure in which a divalent or higher-valent group derived by removing a total of two or more hydrogen atoms from at least one group selected from the group consisting of $R^1$, $R^2$, and $R^3$ (e.g., a divalent group if two hydrogen atoms are removed, or a trivalent group if three hydrogen atoms are removed) is linked to at least one of $R^1$, $R^2$, or $R^3$ of one or more (preferably one to three) other compounds represented by general formula (1) via a divalent or higher-valent group or a single bond.

That is, in the present invention, compounds having a structure represented by general formula (1) are meant to include compounds represented by general formula (1) and compounds having a structure in which a plurality of structures represented by general formula (1) are present in one molecule.

The alkyl groups represented by $R^1$, $R^2$, and $R^3$ in general formula (1) above are linear, branched, or cyclic substituted or unsubstituted alkyl groups. Preferably, the alkyl groups have 1 to 50 carbon atoms, more preferably 1 to 30 carbon atoms, particularly, preferably 1 to 20 carbon atoms. Preferred examples include methyl, ethyl, n-propyl, isopropyl, cyclopropyl, butyl, isobutyl, t-butyl, s-butyl, pentyl, isopentyl, neopentyl, t-pentyl, hexyl, cyclohexyl, heptyl, cyclopentyl, octyl, 2-ethylhexyl, nonyl, decyl, dodecyl, tetradecyl, hexadecyl, octadecyl, eicosyl, docosyl, and triacontyl. More preferred are methyl, ethyl, n-propyl, isopropyl, butyl, isobutyl, t-butyl, s-butyl, pentyl, isopentyl, neopentyl, hexyl, cyclohexyl, octyl, 2-ethylhexyl, dodecyl, hexadecyl, and octadecyl. Even more preferred are methyl, ethyl, n-propyl, isopropyl, butyl, t-butyl, pentyl, isopentyl, hexyl, cyclohexyl, octyl, 2-ethylhexyl, dodecyl, hexadecyl, and octadecyl.

The alkyl groups represented by $R^1$, $R^2$, and $R^3$ may further have a substituent. Examples of substituents include halogen atoms, alkyl groups (including cycloalkyl groups), alkenyl groups (including cycloalkenyl groups and bicycloalkenyl groups), alkynyl groups, aryl groups, cyano groups, hydroxy groups, nitro groups, carboxy groups, alkoxy groups, aryloxy groups, acyloxy groups, carbamoyloxy groups, alkoxycarbonyloxy groups, aryloxycarbonyloxy groups, amino groups (including anilino groups), acylamino groups, aminocarbonylamino groups, alkoxycarbonylamino groups, aryloxycarbonylamino groups, acyl groups, aryloxycarbonyl groups, alkoxycarbonyl groups, and carbamoyl groups.

More specifically, examples of substituents include halogen atoms (e.g., chlorine, bromine, and iodine atoms); alkyl groups (which represent linear, branched, or cyclic substituted or unsubstituted alkyl groups, including alkyl groups (preferably alkyl groups having 1 to 30 carbon atoms, e.g., methyl, ethyl, n-propyl, isopropyl, t-butyl, n-octyl, eicosyl, 2-chloroethyl, 2-cyanoethyl, and 2-ethylhexyl), cycloalkyl groups (preferably substituted or unsubstituted cycloalkyl groups having 3 to 30 carbon atoms, e.g., cyclohexyl, cyclopentyl, and 4-n-dodecylcyclohexyl), bicycloalkyl groups (preferably substituted or unsubstituted bicycloalkyl groups having 5 to 30 carbon atoms, i.e., monovalent groups derived by removing one hydrogen atom from bicycloalkanes having 5 to 30 carbon atoms, e.g., bicyclo[1.2.2]heptan-2-yl and bicyclo[2.2.2]octan-3-yl), and groups having larger numbers of cyclic structures, including tricyclo structures; this definition of alkyl groups also applies to the alkyl groups of the substituents described below (e.g., the alkyl groups of alkylthio groups)); alkenyl groups (including alkenyl groups (preferably substituted or unsubstituted alkenyl groups having 2 to 30 carbon atoms, e.g., vinyl, allyl, prenyl, geranyl, and oleyl), cycloalkenyl groups (preferably substituted or unsubstituted cycloalkenyl groups having 3 to 30 carbon atoms, i.e., monovalent groups derived by removing one hydrogen atom from cycloalkenes having 3 to 30 carbon atoms, e.g., 2-cyclopenten-1-yl and 2-cyclohexen-1-yl), and bicycloalkenyl groups (substituted or unsubstituted bicycloalkenyl groups, preferably substituted or unsubstituted bicycloalkenyl groups having 5 to 30 carbon atoms, i.e., monovalent groups derived by removing one hydrogen atom from bicycloalkenes having one double bond, e.g., bicyclo[2.2.1]hept-2-en-1-yl and bicyclo[2.2.2]oct-2-en-4-yl));

alkynyl groups (preferably substituted or unsubstituted alkynyl groups having 2 to 30 carbon atoms, e.g., ethynyl, propargyl, and trimethylsilylethynyl); aryl groups (preferably substituted or unsubstituted aryl groups having 6 to 30 carbon atoms, e.g., phenyl, p-tolyl, naphthyl, m-chlorophenol, and o-hexadecanoylaminophenyl); heterocyclic groups (preferably monovalent groups derived by removing one hydrogen atom from 5- or 6-membered substituted or unsubstituted aromatic or nonaromatic heterocyclic compounds, more preferably 5- or 6-membered aromatic heterocyclic groups having 3 to 30 carbon atoms, e.g., 2-furanyl, 2-thienyl, 2-pyrimidinyl, and 2-benzothiazolinyl); cyano groups; hydroxy groups; nitro groups; carboxy groups; alkoxy groups (preferably substituted or unsubstituted alkoxy groups having 1 to 32 carbon atoms, e.g., methoxy, ethoxy, isopropoxy, t-butoxy, n-octyloxy, and 2-methoxyethoxy); aryloxy groups (preferably substituted or unsubstituted aryloxy groups having 6 to 30 carbon atoms, e.g., phenoxy, 2-methylphenoxy, 4-t-butylphenoxy, 3-nitrophenoxy, and 2-tetradecanoylaminophenoxy); silyloxy groups (preferably silyloxy groups having 3 to 20 carbon atoms, e.g., trimethylsilyloxy and t-butyldimethylsilyloxy); heterocyclic oxy groups (preferably substituted or unsubstituted heterocyclic oxy groups having 2 to 30 carbon atoms, e.g. 1-phenyltetrazole-5-oxo and 2-tetrahydropyranyloxy); acyloxy groups (preferably formyloxy groups, substituted or unsubstituted alkylcarbonyloxy groups having 2 to 30 carbon atoms, and substituted or unsubstituted arylcarbonyloxy groups having 6 to 30 carbon atoms, e.g., formyloxy, acetyloxy, pivaloyloxy, stearoyloxy, benzoyloxy, and p-methoxyphenylcarbonyloxy); carbamoyloxy groups (preferably substituted or unsubstituted carbamoyloxy groups having 1 to 30 carbon atoms, e.g., N,N-dimethylcarbamoyloxy, N,N-diethylcarbamoyloxy, morpholinocarbonyloxy, N,N-di-n-octylaminocarbonyloxy, and N-n-octylcarbamoyloxy); alkoxycarbonyloxy groups (preferably substituted or unsubstituted alkoxycarbonyloxy groups having 2 to 30 carbon atoms, e.g., methoxycarbonyloxy, ethoxycarbonyloxy, t-butoxycarbonyloxy, and n-octyloxycarbonyloxy); aryloxycarbonyloxy groups (preferably substituted or unsubstituted aryloxycarbonyloxy groups having 7 to 30 carbon atoms, e.g., phenoxycarbonyloxy, p-methoxyphenoxycarbonyloxy, and p-n-hexadecyloxyphenoxycarbonyloxy);

amino groups (preferably amino groups, substituted or unsubstituted alkylamino groups having 1 to 30 carbon atoms, and substituted or unsubstituted anilino groups having 6 to 30 carbon atoms, e.g., amino, methylamino, dimethylamino, anilino, N-methyl-anilino, and diphenylamino); acylamino groups (preferably formylamino groups, substituted or unsubstituted alkylcarbonylamino groups having 1 to 30 carbon atoms, and substituted or unsubstituted arylcarbonylamino groups having 6 to 30 carbon atoms, e.g., formylamino, acetylamino, pivaloylamino, lauroylamino, benzoylamino, and octyloxyphenylcarbonylamino); aminocarbonylamino groups (preferably substituted or unsubstituted aminocarbonylamino groups having 1 to 30 carbon atoms, e.g., carbamylamino, N,N-dimethylaminocarbonylamino, N,N-diethylaminocarbonylamino, and morpholinocarbonylamino); alkoxycarbonylamino groups (preferably substituted or unsubstituted alkoxycarbonylamino groups having 2 to 30 carbon atoms, e.g., methoxycarbonylamino, ethoxycarbonylamino, t-butoxycarbonylamino, n-octadecyloxycarbonylamino, and N-methyl-methoxycarbonylamino); aryloxycarbonylamino groups (preferably substituted or unsubstituted aryloxycarbonylamino groups having 7 to 30 carbon atoms, e.g., phenoxycarbonylamino, p-chlorophenoxycarbonylamino, and m-n-octyloxyphenoxycarbonylamino); sulfamoylamino groups (preferably substituted or unsubstituted sulfamoylamino groups having 0 to 30 carbon atoms, e.g., sulfamoylamino, N,N-dimethylaminosulfonylamino, and N-n-octylaminosulfonylamino); alkylsulfonylamino and arylsulfonylamino groups (preferably substituted or unsubstituted alkylsulfonylamino groups having 1 to 30 carbon atoms and substituted or unsubstituted arylsulfonylamino groups having 6 to 30 carbon atoms, e.g., methylsulfonyl amino, butylsulfonylamino, phenylsulfonylamino, 2,3, 5-trichlorophenylsulfonylamino, and p-methylphenylsulfonylamino);

sulfanyl groups; alkylthio groups (preferably substituted or unsubstituted alkylthio groups having 1 to 30 carbon atoms, e.g., methylthio, ethylthio, and n-hexadecylthio); arylthio groups (preferably substituted or unsubstituted arylthio groups having 6 to 30 carbon atoms, phenylthio, p-chlorophenylthio, and m-methoxyphenylthio); heterocyclic thio groups (preferably substituted or unsubstituted heterocyclic thio groups having 2 to 30 carbon atoms, e.g., 2-benzothiazolylthio and 1-phenyltetrazol-5-ylthio); sulfamoyl groups (preferably substituted or unsubstituted sulfamoyl groups having 0 to 30 carbon atoms, N-ethylsulfamoyl, N-(3-dodecyloxypropyl)sulfamoyl, N,N-dimethylsulfamoyl, N-acetylsulfamoyl, N-benzoylsulfamoyl, and N—(N'-phenylcarbamoyl)sulfamoyl); sulfo groups; alkylsulfinyl and arylsulfinyl groups (preferably substituted or unsubstituted alkylsulfinyl groups having 1 to 30 carbon atoms and substituted or unsubstituted arylsulfinyl groups having 6 to 30 carbon atoms, e.g., methylsulfinyl, ethylsulfinyl, phenylsulfinyl, and p-methylphenylsulfinyl);

alkylsulfonyl and arylsulfonyl groups (preferably substituted or unsubstituted alkylsulfonyl groups having 1 to 30 carbon atoms and substituted or unsubstituted arylsulfonyl groups having 6 to 30 carbon atoms, e.g., methylsulfonyl, ethylsulfonyl, phenylsulfonyl, and p-methylphenylsulfonyl); acyl groups (preferably formyl groups, substituted or unsubstituted alkylcarbonyl groups having 2 to 30 carbon atoms, substituted or unsubstituted arylcarbonyl groups having 7 to 30 carbon atoms, and substituted or unsubstituted heterocyclic carbonyl groups having 4 to 30 carbon atoms in which any of the carbon atoms is attached to the carbonyl group), e.g., acetyl, pivaloyl, 2-chloroacetyl, stearoyl, benzoyl, p-n-octyloxyphenylcarbonyl, 2-pyridylcarbonyl, and 2-furylcarbonyl); aryloxycarbonyl groups (preferably substituted or unsubstituted aryloxycarbonyl groups having 7 to 30 carbon atoms, e.g., phenoxycarbonyl, o-chlorophenoxycarbonyl, m-nitrophenoxycarbonyl, and p-t-butylphenoxycarbonyl); alkoxycarbonyl groups (preferably substituted or unsubstituted alkoxycarbonyl groups having 2 to 30 carbon atoms, e.g., methoxycarbonyl, ethoxycarbonyl, t-butoxycarbonyl, and n-octadecyloxycarbonyl);

carbamoyl groups (preferably substituted or unsubstituted carbamoyl groups having 1 to 30 carbon atoms, e.g., carbamoyl, N-methylcarbamoyl, N,N-dimethylcarbamoyl, N,N-di-n-octylcarbamoyl, and N-(methylsulfonyl)carbamoyl); arylazo and heterocyclic azo groups (preferably substituted or unsubstituted arylazo groups having 6 to 30 carbon atoms and substituted or unsubstituted heterocyclic azo groups having 3 to 30 carbon atoms, e.g., phenylazo, p-chlorophenylazo, and 5-ethylthio-1,3,4-thiadiazol-2-ylazo); imide groups (preferably N-succinimide and N-phthalimide); phosphino groups (preferably substituted or unsubstituted phosphino groups having 2 to 30 carbon atoms, e.g., dimethylphosphino, diphenylphosphino, and methylphenoxyphosphino); phosphinyl groups (preferably substituted or unsubstituted phosphinyl groups having 2 to 30 carbon atoms, e.g., phosphinyl, dioctyloxyphosphinyl, and diethoxyphosphinyl); phosphinyloxy groups (preferably substituted or unsubstituted phosphinyloxy groups having 2 to 30 carbon atoms, e.g., diphenoxyphosphinyloxy and dioctyloxyphosphinyloxy); phosphinylamino groups (preferably substituted or unsubstituted phosphinylamino groups having 2 to 30 carbon atoms, e.g., dimethoxyphosphinylamino and dimethylaminophosphinylamino); and silyl groups (preferably substituted or unsubstituted silyl groups having 3 to 30 carbon atoms, e.g., trimethylsilyl, t-butyldimethylsilyl, and phenyldimethylsilyl).

Of the above substituents, those having hydrogen atoms may have their hydrogen atoms replaced by the above substituents. Examples of such substituents include alkylcarbonylaminosulfonyl groups, arylcarbonylaminosulfonyl groups, alkylsulfonylaminocarbonyl groups, arylsulfonylaminocarbonyl groups, e.g. methylsulfonylaminocarbonyl groups, p-methylphenylsulfonylaminocarbonyl groups, acetylaminosulfonyl groups, and benzoylaminosulfonyl groups.

The aryl groups represented by $R^1$, $R^2$, and $R^3$ represent substituted or unsubstituted aryl groups. Preferably, the aryl groups have 6 to 50 carbon atoms, more preferably 6 to 30 carbon atoms, particularly preferably 6 to 20 carbon atoms. Preferred examples include phenyl, 2-methylphenyl, 3-methylphenyl, 4-methylphenyl, 2-ethylphenyl, 4-ethylphenyl, 2,4-dimethylphenyl, 2,6-dimethyl phenyl, 2,4,6-trimethylphenyl, 1-naphthyl, 2-naphthyl, 2-chlorophenyl, 3-chlorophenyl, 4-chlorophenyl, 2-methoxyphenyl, 3-methoxyphenyl, 4-methoxyphenyl, 2-benzylphenyl, 4-benzylphenyl, 2-methylcarbonylphenyl, and 4-methylcarbonylphenyl.

More preferably, the aryl groups represented by $R^1$, $R^2$, and $R^3$ are phenyl, methylphenyl, 4-methylphenyl, 2-ethylphenyl, 4-ethylphenyl, 2,4-dimethylphenyl, 2,6-dimethylphenyl, 2,4,6-trimethylphenyl, 1-naphthyl, 2-naphthyl, 2-chlorophenyl, 4-chlorophenyl, 2-methoxyphenyl, 3-methoxyphenyl, 4-methoxyphenyl, 2-benzylphenyl, or 4-benzylphenyl, particularly preferably phenyl.

The above aryl groups represented by $R^1$, $R^2$, and $R^3$ may further have a substituent. Examples of substituents include the substituents listed above that the alkyl groups represented by $R^1$ and $R^3$ may have.

The alkoxy groups represented by $R^1$ and $R^2$ represent linear, branched, or cyclic substituted or unsubstituted alkoxy groups. Preferably, the alkoxy groups have 1 to 50 carbon atoms, more preferably 1 to 30 carbon atoms, particularly preferably 1 to 20 carbon atoms. Preferred examples include methoxy, ethoxy, n-propoxy, isopropoxy, cyclopropoxy, butoxy, isobutoxy, t-butoxy, s-butoxy, pentyloxy, isopentyloxy, t-pentyloxy, hexyloxy, cyclohexyloxy, heptyloxy, cyclopentyloxy, octyloxy, 2-ethylhexyloxy, nonyloxy, decyloxy, dodecyloxy, tetradecyloxy, hexadecyloxy, octadecyloxy, eicosyloxy, docosyloxy, and triacontyloxy, more preferably methoxy, ethoxy, n-propoxy, iso-propoxy, butoxy, isobutoxy, t-butoxy, s-butoxy, pentyloxy, isopentyloxy, neopentyloxy, hexyloxy, cyclohexyloxy, octyloxy, 2-ethylhexyloxy, dodecyloxy, hexadecyloxy, and octadecyloxy, particularly preferably methoxy, ethoxy, n-propoxy, isopropoxy, t-butoxy, pentyloxy, isopentyloxy, hexyloxy, cyclohexyloxy, octyloxy, 2-ethylhexyloxy, dodecyloxy, hexadecyloxy, and octadecyloxy.

The above alkoxy groups represented by $R^1$ and $R^2$ may further have a substituent. Examples of substituents include the substituents listed above that the alkyl groups represented by $R^1$, $R^2$, and $R^3$ may have.

The aryloxy groups represented by $R^1$ and $R^2$ represent substituted or unsubstituted aryloxy groups. Preferably, the aryloxy groups have 6 to 50 carbon atoms, more preferably 6 to 30 carbon atoms, particularly preferably 6 to 20 carbon atoms. Preferred examples include phenoxy, 2-methylphenoxy, 3-methylphenoxy, 4-methylphenoxy, 2-ethylphenoxy, 4-ethylphenoxy, 2,4-dimethylphenoxy, 2,4-di-t-butylphenoxy, 2,6-di-t-butylphenoxy, 2,6-dimethylphenoxy, 2,6-di-t-butyl-4-methylphenoxy, 2,4,6-trimethylphenoxy, 2,4,6-tri-t-butylphenoxy, 1-naphthyloxy, 2-naphthyloxy, 2-chlorophenoxy, 3-chlorophenoxy, 4-chlorophenoxy, ethoxyphenoxy, 3-methoxyphenoxy, 4-methoxyphenoxy, 2-benzylphenoxy, 4-benzylphenoxy, 2-methyl carbonylphenoxy, and 4-methyl carbonylphenoxy.

More preferred examples include phenyl, 2,4-di-t-butylphenoxy, and 2,4,6-tri-t-butylphenoxy.

The above aryloxy groups represented by $R^1$ and $R^2$ may further have a substituent. Examples of substituents include the substituents listed above that the alkyl groups represented by $R^1$, $R^2$, and $R^3$ may have.

From the viewpoint of the compatibility between the resin and the phosphite-based antioxidant, it is preferred that, in general formula (1), $R^1$ and $R^2$ be alkoxy groups or aryloxy groups, and $R^3$ be an alkyl group or an aryl group.

Examples of divalent or higher-valent groups that serve as a linking group in the compound having a structure represented by general formula (1) include divalent or higher-valent groups derived by removing one or more hydrogen atoms from the substituents listed above for the alkyl groups represented by $R^1$, $R^2$, and $R^3$ (divalent groups if one hydrogen atom is removed from the substituents, or trivalent groups if two hydrogen atoms are removed from the substituents) and combinations thereof. These divalent or higher-valent groups are preferably divalent to hexavalent, more preferably divalent to tetravalent. The above divalent or higher-valent groups are preferably organic groups.

The above divalent or higher-valent groups may further have a substituent. Examples of substituents include the substituents listed above that the alkyl groups represented by $R^1$, $R^2$, and $R^3$ may have.

The above divalent or higher-valent groups preferably have a molecular weight of 10 to 1,000.

Preferred of the above divalent or higher-valent groups and single bonds are single bonds and divalent or higher-valent groups derived by removing one or more hydrogen atoms from amino groups, alkyl groups, aryl groups, bis-aryl groups (arylaryl groups), arylalkylaryl groups, aryloxyaryl groups, alkoxyalkyl groups, alkoxyaryl groups, and alkylaryl groups.

If the compound having a structure represented by general formula (1) is a compound in which a plurality of structures represented by general formula (1) are present in one molecule, the compound preferably has, in one molecule, 2 to 20 phosphorus atoms, more preferably 2 to 10 phosphorus atoms, even more preferably 2 to 5 phosphorus atoms.

Specific examples of compounds represented by general formula (1) above are given below, although these examples are not intended to limit the present invention.

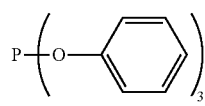 1-1
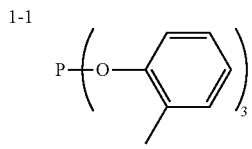 1-2
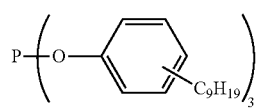 1-3
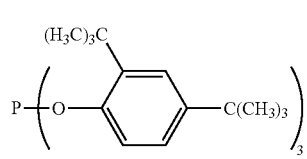 1-4
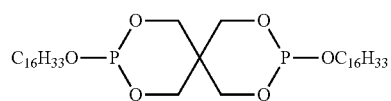 1-5
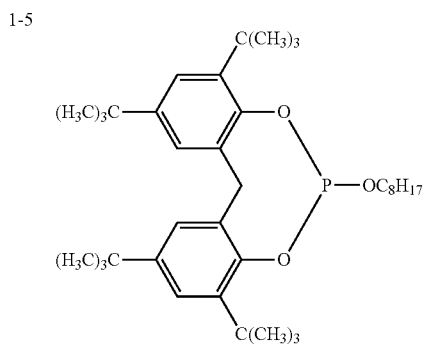 1-6
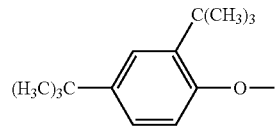 1-7
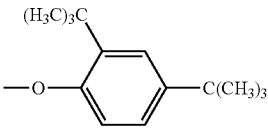 1-8
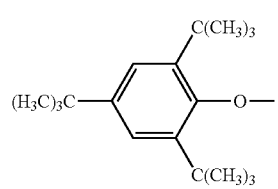 1-9
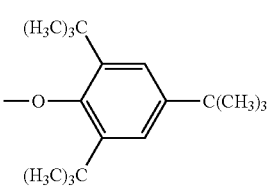
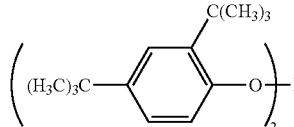 1-10
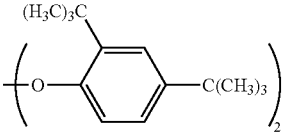 1-11
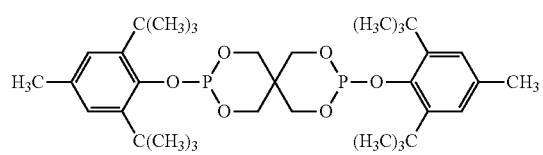
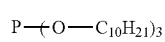
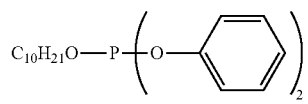 1-12
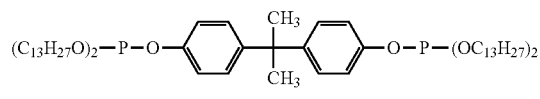 1-13

-continued 1-14
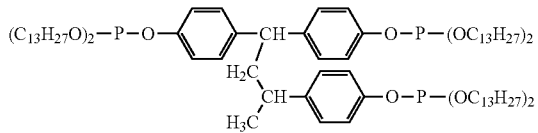

1-15
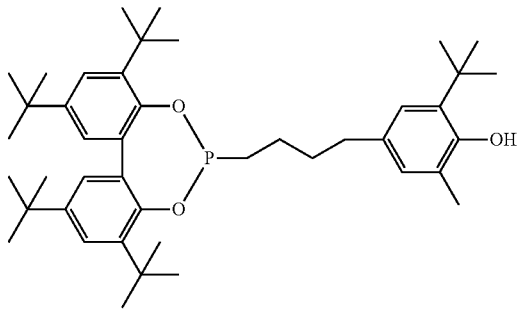

1-16
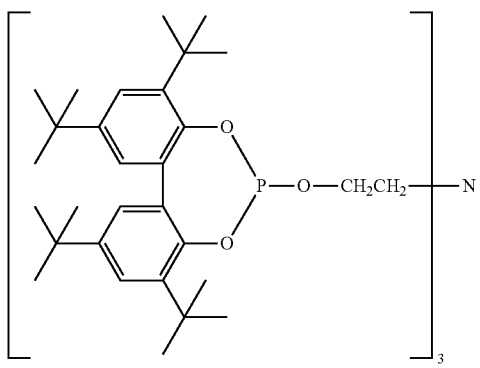

1-17
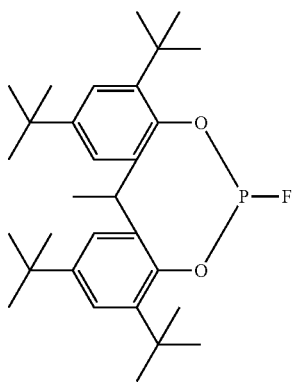

1-18
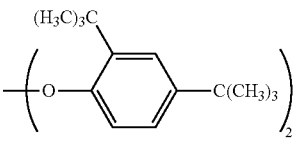

1-19
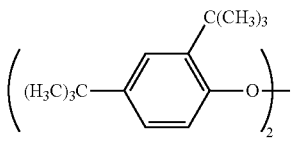

1-20
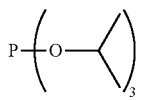

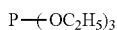

1-21
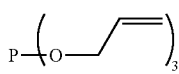

1-22
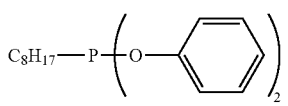

1-23
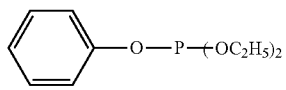

Other compounds suitable for use as the compound having a structure represented by general formula (1) include phosphorous acid ester compounds described in JP2011-527357A.

Thioether-Based Antioxidant

The thioether-based antioxidant is preferably a compound having a structure represented by general formula (2):

$$R^4\text{—S—}R^5 \quad \text{formula (2)}$$

In general formula (2), $R^4$ and $R^5$ represent an alkyl group and may be linked to each other via a divalent or higher-valent group or a single bond.

In the present invention, compounds having a structure represented by general formula (2) includes, in addition to compounds represented by general formula (2), compounds (iii) and (iv) below.

(iii) Compounds having a structure in which a monovalent group derived by removing one hydrogen atom from $R^4$ or $R^5$ is linked to $R^4$ and/or $R^5$ of one or more (preferably one to three) other compounds represented by general formula (2) via a divalent or higher-valent group or a single bond; and (iv) compounds having a structure in which a divalent or higher-valent group derived by removing a total of two or more hydrogen atoms from at least one group selected from the group consisting of $R^4$ and $R^5$ (e.g., a divalent group if two hydrogen atoms are removed, or a trivalent group if three hydrogen atoms are removed) is linked to $R^4$ and/or or $R^5$ of one or more (preferably one to three) other compounds represented by general formula (2) via a divalent or higher-valent group or a single bond.

That is, in the present invention, compounds having a structure represented by general formula (2) are meant to include compounds represented by general formula (2) and compounds having a structure in which a plurality of structures represented by general formula (2) are present in one molecule.

The alkyl groups represented by $R^4$ and $R^5$ represent linear, branched, or cyclic substituted or unsubstituted alkyl groups. Preferably, the alkyl groups have 1 to 50 carbon atoms, more preferably 2 to 30 carbon atoms, particularly preferably 2 to 20 carbon atoms, Preferred examples include methyl, ethyl, n-propyl, isopropyl, cyclopropyl, butyl, isobutyl, t-butyl, s-butyl, pentyl, isopentyl, neopentyl, t-pentyl, hexyl, cyclohexyl, heptyl, cyclopentyl, octyl, 2-ethylhexyl, nonyl, decyl, dodecyl, tetradecyl, hexadecyl, octadecyl, eicosyl, docosyl, and triacontyl. More preferred are methyl, ethyl, n-propyl, isopropyl, butyl, isobutyl, t-butyl, s-butyl, pentyl, isopentyl, neopentyl, hexyl, cyclohexyl, octyl, 2-ethylhexyl, dodecyl, hexadecyl, and octadecyl. Particularly preferred are methyl, ethyl, n-propyl, isopropyl, butyl, t-butyl, pentyl, isopentyl, hexyl, cyclohexyl, octyl, 2-ethylhexyl, dodecyl, hexadecyl, and octadecyl.

Examples of substituents for the substituted alkyl groups represented by $R^4$ and $R^5$ include the substituents listed above that the alkyl groups represented by $R^1$, $R^2$, and $R^3$ in general formula (1) may have.

Of the substituted alkyl groups represented by $R^4$ and $R^5$, alkoxycarbonylalkyl groups are preferred. The alkoxycarbonyl groups of the alkoxycarbonylalkyl groups preferably have 2 to 50 carbon atoms, more preferably 5 to 30 carbon atoms, particularly preferably 9 to 20 carbon atoms.

The divalent or higher-valent group serving as a linking group in the compound having a structure represented by general formula (2) is similar to the divalent or higher-valent group described as a linking group in general formula (1) above, and a preferred range is also similar.

Specific examples of compounds represented by general formula (2) above are given below, although these examples are not intended to limit the present invention.

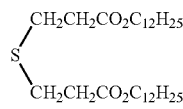

2-1

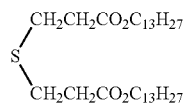

2-2

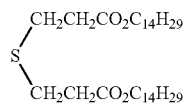

2-3

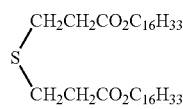

2-4

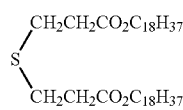

2-5

2-6

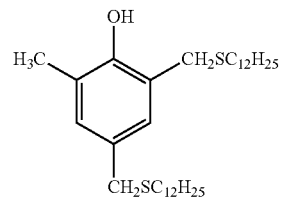

2-7

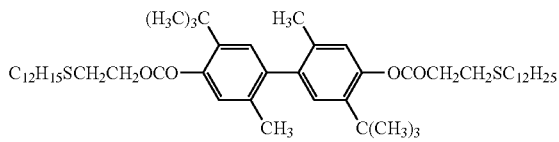

2-8

These components (c) may be used alone or in combination.

In the present invention, the amount of the component (c) is preferably 0.15% to 4% by mass, more preferably 0.25% to 4% by mass, based on 100% by mass of all components forming the resin layer (A). If the amount of the component (c) is not less than the above lower limit, the bending durability can be further improved. On the other hand, if the amount of the component (c) is not more than the above upper limit, the bending hardness can be further improved.

The resin layer (A) may include components other than the components (a) to (c) as long as they do not interfere with the advantages of the present invention. Examples of such components include plasticizers, light stabilizers, lubricants, antistatic agents, release agents, and colorants (e.g., pigments and dyes)

Resin Composition for Covering Flexible Tube Substrate for Endoscope

The flexible tube according to the present invention is preferably produced using a resin composition for covering a flexible tube substrate for an endoscope according to the present invention. The resin composition for covering a flexible tube substrate for an endoscope according to the present invention includes a thermoplastic resin (a) including at least one of a polyamide, a polyurethane, a polyester, a polystyrene, or an acrylic resin and having a tensile strength at 10% elongation of 10 MPa or more and a hindered amine compound (b) having a molecular weight of 500 or more.

The resin composition for covering a flexible tube substrate for an endoscope according to the present invention can be prepared as usual. The amounts of the individual components (solid components) in the resin composition for covering a flexible tube substrate for an endoscope according to the present invention are the same as those in the flexible tube according to the present invention.

Although an electronic endoscope for observation of an image of the condition of a subject captured using an imaging device has been described by way of example in the foregoing embodiment, the present invention is not limited thereto, but may also be applied to an endoscope for observation of the condition of a subject using an optical image guide.

Endoscopic Medical Device

The flexible tube for an endoscope according to the present invention is not limited to endoscope applications, but can also be applied to a wide variety of endoscopic medical devices. For example, the flexible tube according to the present invention can be applied to an endoscope equipped with a clip or wire at the distal end thereof or to a device equipped with a basket or brush and provides its superior effect. Endoscopic medical devices are meant to include a wide variety of flexible medical and diagnostic devices for introduction and use in a body, including medical devices having an endoscope as a basic structure, as described above, and remotely operated medical devices.

EXAMPLES

The present invention will now be described in more detail with reference to the following examples, although these examples should not be construed as limiting the invention.

EXAMPLES AND COMPARATIVE EXAMPLES

Resin compositions were prepared by mixing together a thermoplastic resin (a), a hindered amine compound (b), and an antioxidant (c) in the amounts (in parts by mass) shown in Table 1 below. Each of the resin compositions was introduced into a twin-screw kneader (the trade name KZW15-30MG available from Technovel Corporation) in which the barrel temperature and the die temperature were set to a temperature 20° C. above the melting point of the thermoplastic resin (a) and was kneaded at a screw rotational speed of 100 rpm. A molten resin strand ejected from the twin-screw kneader was cooled in a water bath and was then cut with a pelletizer to form a pelletized sample. This sample was compression-molded (at a pressure of 50 MPa) at a temperature 5° C. above the melting point of the thermoplastic resin (a) to form a resin sheet having a length of 100 mm, a width of 100 mm, and a thickness of 2 mm.

Tensile Strength at 10% Elongation

A pelletized sample prepared from the thermoplastic resin (a) alone in the same manner as above was compression-molded at a temperature 5° C. above the melting point to obtain a resin sheet of the thermoplastic resin (a) having a length of 100 mm, a width of 100 mm, and a thickness of 2 mm. A No. 1 dumbbell-shaped specimen was cut out and was subjected to a tensile test in accordance with JIS K 6251:2017 to determine the strength at an elongation of 10% (the strength at which the length of the specimen was 44 mm when the specimen was stretched in the machine direction at a chuck-to-chuck distance of 40 mm).

Surface Hardness

Four resin sheets (thickness: 8 mm) of the thermoplastic resin (a) were stacked together, and the surface hardness was determined with a rubber hardness tester in accordance with JIS K 6253-3:2012.

Test Example 1 (Moldability Test)

Each of the pelletized samples prepared as described above and containing the components (a) to (c) was introduced into a single-screw extruder (the trade name Laho Plastomill model M available from Toyo Seiki Seisaku-sho, Ltd.) in which the barrel temperature and the die temperature were set to a temperature 20° C. above the melting point of the thermoplastic resin (a). The ejection speed was set to 1 kg/hr, and the sample was ejected in a molten state from the die. The masses of the sample ejected during the period from 5 to 6 minutes and the period from 60 to 61 minutes upon starting of ejection were measured. The ejected mass fraction was calculated from the following equation and was evaluated for the moldability of the sample on the following evaluation scale, where "C" or higher is satisfactory in this test.

Ejected mass fraction (%)={mass (g) of sample ejected during period from 60 to 61 minutes upon starting of ejection/mass (g) of sample ejected during period from 5 to 6 minutes upon starting of ejection}×100

Evaluation Scale
A: The ejected mass fraction was 99% or more, to 101% or less.
B: The ejected mass fraction was 97% to less than 99%, or more than 101% to 103%.
C: The ejected mass fraction was 95% to less than 97%, or more than 103% to 105%.
D: The ejected mass fraction was less than 95%, or more than 105%.

Test Example 2 (Bending Hardness Test)

Each of the pelletized samples prepared as described above and containing the components (a) to (c) was compression-molded at a temperature 5° C. above the melting point to obtain a resin sheet having a length of 100 mm, a width of 100 mm, and a thickness of 4 mm. The resin sheet was then cut to obtain a test specimen having a length of 80 mm, a width of 10 mm, and a thickness of 4 mm. This test specimen was subjected to a bending test at a room temperature of 23° C. and a test speed of 2 mm/min in accordance with JIS K 7171-1:2016 (Method A) to determine the flexural modulus of elasticity. The resulting flexural modulus of elasticity (MPa) was evaluated for bending hardness on the following evaluation scale, where "C" or higher is satisfactory in this test.

Evaluation Scale
A: 400 MPa to less than 1,000 MPa
B: 250 MPa to less than 400 MPa, or 1,000 MPa to less than 1,500 MPa
C: 100 MPa to less than 250 MPa, or 1,500 MPa to less than 2,000 MPa
D: less than 100 MPa, or 2,000 MPa or more Test Example 3 (Bending Durability Test)

Flexible tubes for endoscopes shown in FIG. 2 were produced. Specifically, each of the pelletized samples prepared as described above and containing the components (a) to (c) was extruded so as to cover a flexible tube substrate formed of stainless steel (SUS) 314 and having an outer diameter of 4.0 mm and a length of 60 cm such that the layer thickness was 300 μm. Thus, a flexible tube for an endoscope was produced.

The resulting flexible tube for an endoscope was repeatedly bent back and forth in the center in the longitudinal direction so as to be U-shaped with a radius of curvature of 5 cm. The number of bending cycles to peeling between the flexible tube substrate and the resin layer was evaluated on the following evaluation scale, where "C" or higher is satisfactory.

Evaluation Scale
A: 10,000 cycles or more
B: 2,000 cycles to less than 10,000 cycles
C: 100 cycles to less than 2,000 cycles
D: less than 100 cycles Test Example 4 (Sterilization Durability Test 1)

Flexible tubes for endoscopes shown in FIG. 2 were produced as in Test Example 3. The resin layer was stripped from each of the flexible tube substrates, and a test specimen with a size of 1 cm×10 cm was cut from the resin layer. This test specimen was subjected to low-temperature plasma sterilization treatment on the advanced course of an STER-RAD (registered trademark) NX (trade name, available from Johnson & Johnson). This sterilization treatment was performed 100 times for each test specimen. After testing (after hydrogen peroxide plasma treatment), the test specimen was dried at 23° C. and 50% RH (relative humidity) for 24 hours and was then subjected to a tensile test with a TENSILON RTF-1210 universal material testing machine (trade name, available from A&D Company, Limited). The test specimen was evaluated on the following evaluation scale (an elongation of 100% means stretching to twice the original length), where "C" or higher is satisfactory in this test.

Evaluation Scale

A: The test specimen was not broken after a tensile test at an elongation of 300%.

B: The test specimen was not broken after a tensile test at an elongation of 200%, but was broken after a tensile test at an elongation of 300%.

C: The test specimen was not broken after a tensile test at an elongation of 100%, but was broken after a tensile test at an elongation of 200%.

D: The test specimen was broken after a tensile test at an elongation of 100%.

Test Example 5 (Sterilization Durability Test 2)

Flexible tubes for endoscopes were produced as in Test Example 4. The resin layer was stripped from each of the flexible tube substrates, and a test specimen with a size of 1 cm×10 cm was cut from the resin layer. This test specimen was subjected to hydrogen peroxide gas sterilization treatment with a V-PRO (registered trademark) 60 (trade name, available from Steris Inc.). This sterilization treatment was performed 100 times for each test specimen. After testing (after hydrogen peroxide gas treatment), the test specimen was dried at 23° C. and 50% RH (relative humidity) for 24 hours and was then subjected to a tensile test with a TENSILON RTF-1210 universal material testing machine (trade name, available from A&D Company, Limited). The test specimen was evaluated on the following evaluation scale (an elongation of 100% means stretching to twice the original length), where "C" or higher is satisfactory in this test.

Evaluation Scale

A: The test specimen was not broken after a tensile test at an elongation of 300%.

B: The test specimen was not broken after a tensile test at an elongation of 200%, but was broken after a tensile test at an elongation of 300%.

C: The test specimen was not broken after a tensile test at an elongation of 100%, but was broken after a tensile test at an elongation of 200%.

D: The test specimen was broken after a tensile test at an elongation of 100%.

TABLE 1

| | | Example 1 | Example 2 | Example 3 | Example 4 | Example 5 | Example 6 |
|---|---|---|---|---|---|---|---|
| Component (a) | Species | (A-1) | (A-2) | (A-3) | (A-4) | (A-5) | (A-6) |
| | | PA11 | PA12 | PA1010 | PA1012 | Amorphous PA | Amorphous PA |
| | Tensile strength at 10% elongation (MPa) | 21 | 23 | 44 | 38 | 42 | 58 |
| | Amount (parts by mass) | 98.5 | 98.5 | 98.5 | 98.5 | 98.5 | 98.5 |
| Component (b) | Species | (B-1) | (B-1) | (B-1) | (B-1) | (B-1) | (B-1) |
| | Type | N-R | N-R | N-R | N-R | N-R | N-R |
| | Molecular weight | 3,500 | 3,500 | 3,500 | 3,500 | 3,500 | 3,500 |
| | Amount (parts by mass) | 1.0 | 1.0 | 1.0 | 1.0 | 1.0 | 1.0 |
| Component (c) | Species | (C-1) | (C-1) | (C-1) | (C-1) | (C-1) | (C-1) |
| | Amount (parts by mass) | 0.5 | 0.5 | 0.5 | 0.5 | 0.5 | 0.5 |
| Molding stability | | A | A | A | A | A | A |
| Bending hardness | | A | A | B | B | B | C |
| Bending durability | | A | A | B | B | B | C |
| Sterilization Durability 1 | | A | A | B | B | A | B |
| Sterilization Durability 2 | | A | A | B | B | A | B |

| | | Example 7 | Example 8 | Example 9 | Example 10 |
|---|---|---|---|---|---|
| Component (a) | Species | (A-7) | (A-8) | (A-9) | (A-10) |
| | | PA elastomer | PA elastomer | Aliphatic TPU | Aliphatic TPU |
| | Tensile strength at 10% elongation (MPa) | 17 | 23 | 15 | 17 |
| | Amount (parts by mass) | 98.5 | 98.5 | 98.5 | 98.5 |
| Component (b) | Species | (B-1) | (B-1) | (B-1) | (B-1) |
| | Type | N-R | N-R | N-R | N-R |
| | Molecular weight | 3,500 | 3,500 | 3,500 | 3,500 |
| | Amount (parts by mass) | 1.0 | 1.0 | 1.0 | 1.0 |
| Component (c) | Species | (C-1) | (C-1) | (C-1) | (C-1) |
| | Amount (parts by mass) | 0.5 | 0.5 | 0.5 | 0.5 |
| Molding stability | | A | A | A | A |
| Bending hardness | | A | A | A | A |
| Bending durability | | A | A | A | A |
| Sterilization Durability 1 | | A | A | B | B |
| Sterilization Durability 2 | | B | A | B | B |

TABLE 1-continued

|  |  | Example 11 | Example 12 | Example 13 | Example 14 | Example 15 | Example 16 |
|---|---|---|---|---|---|---|---|
| Component (a) | Species | (A-11) | (A-12) | (A-13) | (A-14) | (A-15) | (A-16) |
|  |  | Aromatic TPU | C6-TPU | TPEE | TPEE | Naphthalene TPEE | Styrene |
|  | Tensile strength at 10% elongation (MPa) | 27 | 39 | 14 | 24 | 19 | 10 |
|  | Amount (parts by mass) | 98.5 | 98.5 | 98.5 | 98.5 | 98.5 | 98.5 |
| Component (b) | Species | (B-1) | (B-1) | (B-1) | (B-1) | (B-1) | (B-1) |
|  | Type | N-R | N-R | N-R | N-R | N-R | N-R |
|  | Molecular weight | 3,500 | 3,500 | 3,500 | 3,500 | 3,500 | 3,500 |
|  | Amount (parts by mass) | 1.0 | 1.0 | 1.0 | 1.0 | 1.0 | 1.0 |
| Component (c) | Species | (C-1) | (C-1) | (C-1) | (C-1) | (C-1) | (C-1) |
|  | Amount (parts by mass) | 0.5 | 0.5 | 0.5 | 0.5 | 0.5 | 0.5 |
| Molding stability |  | A | A | A | A | A | A |
| Bending hardness |  | A | B | C | A | A | C |
| Bending durability |  | B | A | B | B | A | B |
| Sterilization Durability 1 |  | B | A | A | A | A | A |
| Sterilization Durability 2 |  | B | A | B | A | A | C |

|  |  | Example 17 | Example 18 | Example 19 | Example 20 |
|---|---|---|---|---|---|
| Component (a) | Species | (A-17) | (A-1) | (A-1) | (A-1) |
|  |  | Acrylic | PA11 | PA11 | PA11 |
|  | Tensile strength at 10% elongation (MPa) | 14 | 21 | 21 | 21 |
|  | Amount (parts by mass) | 98.5 | 98.5 | 98.5 | 98.5 |
| Component (b) | Species | (B-1) | (B-2) | (B-3) | (B-4) |
|  | Type | N-R | N-H | N-H | N-R |
|  | Molecular weight | 3,500 | 3,000 | 2,300 | 2,286 |
|  | Amount (parts by mass) | 1.0 | 1.0 | 1.0 | 1.0 |
| Component (c) | Species | (C-1) | (C-1) | (C-1) | (C-1) |
|  | Amount (parts by mass) | 0.5 | 0.5 | 0.5 | 0.5 |
| Molding stability |  | A | A | A | A |
| Bending hardness |  | A | A | A | A |
| Bending durability |  | B | A | A | A |
| Sterilization Durability 1 |  | A | B | B | A |
| Sterilization Durability 2 |  | B | C | C | A |

|  |  | Example 21 | Example 22 | Example 23 | Example 24 | Example 25 | Example 26 |
|---|---|---|---|---|---|---|---|
| Component (a) | Species | (A-1) | (A-1) | (A-1) | (A-1) | (A-1) | (A-1) |
|  |  | PA11 | PA11 | PA11 | PA11 | PA11 | PA11 |
|  | Tensile strength at 10% elongation (MPa) | 21 | 21 | 21 | 21 | 21 | 21 |
|  | Amount (parts by mass) | 98.5 | 98.5 | 98.5 | 98.5 | 98.5 | 98.5 |
| Component (b) | Species | (B-5) | (B-6) | (B-7) | (B-8) | (B-9) | (B-10) |
|  | Type | N-OR | N-R | N-H | N-R | N-H | N-OR |
|  | Molecular weight | 2,261 | 2,000 | 1,900 | 847 | 791 | 681 |
|  | Amount (parts by mass) | 1.0 | 1.0 | 1.0 | 1.0 | 1.0 | 1.0 |
| Component (c) | Species | (C-1) | (C-1) | (C-1) | (C-1) | (C-1) | (C-1) |
|  | Amount (parts by mass) | 0.5 | 0.5 | 0.5 | 0.5 | 0.5 | 0.5 |
| Molding stability |  | A | A | A | A | A | A |
| Bending hardness |  | A | A | A | A | A | A |
| Bending durability |  | A | A | A | A | A | A |
| Sterilization Durability 1 |  | A | A | B | B | C | B |
| Sterilization Durability 2 |  | A | A | C | B | C | B |

|  |  | Example 27 | Example 28 | Example 29 | Example 30 |
|---|---|---|---|---|---|
| Component (a) | Species | (A-1) | (A-1) | (A-1) | (A-1) |
|  |  | PA11 | PA11 | PA11 | PA11 |
|  | Tensile strength at 10% elongation (MPa) | 21 | 21 | 21 | 21 |
|  | Amount (parts by mass) | 98.5 | 99.4 | 99.0 | 96.5 |
| Component (b) | Species | (B-11) | (B-1) | (B-1) | (B-1) |
|  | Type | N-R | N-R | N-R | N-R |
|  | Molecular weight | 509 | 3,500 | 3,500 | 3,500 |
|  | Amount (parts by mass) | 1.0 | 0.1 | 0.5 | 3.0 |
| Component (c) | Species | (C-1) | (C-1) | (C-1) | (C-1) |
|  | Amount (parts by mass) | 0.5 | 0.5 | 0.5 | 0.5 |
| Molding stability |  | A | A | A | A |
| Bending hardness |  | A | A | A | A |
| Bending durability |  | A | A | A | A |
| Sterilization Durability 1 |  | C | B | A | A |
| Sterilization Durability 2 |  | C | B | A | A |

TABLE 1-continued

|  |  | Example 31 | Example 32 | Example 33 | Example 34 | Example 35 | Example 36 |
|---|---|---|---|---|---|---|---|
| Component (a) | Species | (A-1) PA11 | (A-1) PA11 | (A-1) PA11 | (A-1) PA11 | (A-1) PA11 | (A-1) PA11 |
|  | Tensile strength at 10% elongation (MPa) | 21 | 21 | 21 | 21 | 21 | 21 |
|  | Amount (parts by-mass) | 94.5 | 89.5 | 98.5 | 98.5 | 98.5 | 98.5 |
| Component (b) | Species | (B-1) | (B-1) | (B-1) | (B-1) | (B-1) | (B-1) |
|  | Type | N-R | N-R | N-R | N-R | N-R | N-R |
|  | Molecular weight | 3,500 | 3,500 | 3,500 | 3,500 | 3,500 | 3,500 |
|  | Amount (parts by mass) | 5.0 | 10.0 | 1.0 | 1.0 | 1.0 | 1.0 |
| Component (c) | Species | (C-1) | (C-1) | (C-2) | (C-3) | (C-4) | (C-5) |
|  | Amount (parts by-mass) | 0.5 | 0.5 | 0.5 | 0.5 | 0.5 | 0.5 |
| Molding stability |  | A | B | A | A | A | A |
| Bending hardness |  | A | B | A | A | A | A |
| Bending durability |  | B | C | A | A | A | C |
| Sterilization Durability 1 |  | A | A | A | A | A | A |
| Sterilization Durability 2 |  | A | A | A | A | A | A |

|  |  | Example 37 | Example 38 | Example 39 | Example 40 | Example 41 |
|---|---|---|---|---|---|---|
| Component (a) | Species | (A-1) PA11 | (A-1) PA11 | (A-1) PA11 | (A-1) PA11 | (A-1) PA11 |
|  | Tensile strength at 10% elongation (MPa) | 21 | 21 | 21 | 21 | 21 |
|  | Amount (parts by mass) | 98.9 | 98.9 | 98.8 | 98.0 | 98.0 |
| Component (b) | Species | (B-1) | (B-1) | (B-1) | (B-1) | (B-1) |
|  | Type | N-R | N-R | N-R | N-R | N-R |
|  | Molecular weight | 3,500 | 3,500 | 3,500 | 3,500 | 3,500 |
|  | Amount (parts by mass) | 1.0 | 1.0 | 1.0 | 1.0 | 1.0 |
| Component (c) | Species | — | (C-1) | (C-1) | (C-1) | (C-1) |
|  | Amount (parts by mass) |  | 0.1 | 0.2 | 1.0 | 5.0 |
| Molding stability |  | C | C | B | A | A |
| Bending hardness |  | A | A | A | A | C |
| Bending durability |  | C | C | B | A | A |
| Sterilization Durability 1 |  | A | A | A | A | A |
| Sterilization Durability 2 |  | C | A | A | A | A |

TABLE 2

|  |  | Comparative Example 1 | Comparative Example 2 | Comparative Example 3 | Comparative Example 4 | Comparative Example 5 | Comparative Example 6 |
|---|---|---|---|---|---|---|---|
| Component (a) | Species | (A-1) PA11 | (A-1) PA11 | (A-18) TPEE | (A-19) PA elastomer | (A-20) Polyolefin | (A-21) POM |
|  | Tensile strength at 10% elongation (MPa) | 21 | 21 | 8 | 6 | 12 | 22 |
|  | Amount (parts by mass) | 99.5 | 98.5 | 98.5 | 98.5 | 98.5 | 98.5 |
| Component (b) | Species | — | (B-12) | (B-1) | (B-1) | (B-1) | (B-1) |
|  | Type |  | N-H | N-R | N-R | N-R | N-R |
|  | Molecular weight |  | 481 | 3,500 | 3,500 | 3,500 | 3,500 |
|  | Amount (parts by mass) |  | 1.0 | 1.0 | 1.0 | 1.0 | 1.0 |
| Component (c) | Species | (C-1) | (C-1) | (C-1) | (C-1) | (C-1) | (C-1) |
|  | Amount (parts by mass) | 0.5 | 0.5 | 0.5 | 0.5 | 0.5 | 0.5 |
| Molding stability |  | B | A | A | A | C | A |
| Bending hardness |  | A | A | D | D | A | A |
| Bending durability |  | A | A | A | A | D | D |
| Sterilization Durability 1 |  | D | D | A | A | A | D |
| Sterilization Durability 2 |  | D | D | D | D | D | D |

Description of Terms in Tables
Thermoplastic Resins (a)
(A-1) Polyamide 11 (the trade name "Rilsan BMN O" available from Arkema Inc., tensile strength at 10% elongation: 21 MPa, surface hardness: 68D, melt volume rate: 11 cm$^3$/10 min)
(A-2) Polyamide 12 (the trade name "Vestamid L1940" available from Daicel-Evonik Ltd., tensile strength at 10% elongation: 23 MPa, surface hardness: 72D, melt volume rate: 8 cm$^3$/10 min)
(A-3) Polyamide 1010 (the trade name "Vestamid Terra DS16" available from Daicel-Evonik Ltd., tensile strength at 10% elongation: 44 MPa, surface hardness: 78D, melt volume rate: 16 cm$^3$/10 min)
(A-4) Polyamide 1012 (the trade name "Vestamid Terra DD16" available from Evonik, tensile strength at 10% elongation: 38 MPa, surface hardness: 76D, melt volume rate: 14 cm$^3$/10 min)
(A-5) Amorphous polyamide (the trade name "Rilsan Clear 300Hi" available from Arkema Inc., tensile strength at 10% elongation: 42 MPa, surface hardness: 77D, melt volume rate: 16 cm$^3$/10 min)
(A-6) Amorphous polyamide (the trade name "Trogamid CX7323" available from Daicel-Evonik Ltd., tensile strength at 10% elongation: 58 MPa, surface hardness: 81D, melt volume rate: 23 cm³/10 min)

(A-7) Polyamide elastomer (the trade name "Pebax 7233" available from Arkema tensile strength at 10% elongation: 17 MPa, surface hardness: 69D, melt volume rate: 4 cm³/10 min)

(A-8) Polyamide elastomer (the trade name "Pebax Rnew 80R53" available from Arkema Inc., tensile strength at 10% elongation: 23 MPa, surface hardness: 73D, melt volume rate: 5 cm³/10 min)

(A-9) Aliphatic ether-based polyurethane having tetramethyleneoxy structure as soft segments (the trade name "Tecoflex EG-72D" available from Lubrizol Corporation, tensile strength at 10% elongation: 15 MPa, surface hardness: 67D, melt volume rate: 3 cm³/10 min)

(A-10) Aliphatic carbonate-based polyurethane (the trade name "Carbothane PC-3572D" available from Lubrizol Corporation, tensile strength at 10% elongation: 17 MPa, surface hardness: 69D, melt volume rate: 7 cm³/10 min)

(A-11) Aromatic ether-based polyurethane having poly(tetramethyleneoxy) structure as soft segments (the trade name "Miractran E574PNAT" available from Nippon Polyurethane Industry Co., Ltd., tensile strength at 10% elongation: 27 MPa, surface hardness: 74D, melt volume rate: 6 cm³/10 min)

(A-12) Aromatic ether-based polyurethane having poly(hexamethyleneoxy) structure as soft segments (the trade name "Isoplast 2510" available from Lubrizol Corporation, tensile strength at 10% elongation: 39 MPa, surface hardness: 76D, melt volume rate: 8 cm³/10 min)

(A-13) Polyester elastomer (the trade name "Hytrel 5557" available from DuPont-Toray Co., Ltd., tensile strength at 10% elongation: 14 MPa, surface hardness: 55D, melt volume rate: 8 cm³/10 min)

(A-14) Polyester elastomer (the trade name "Hytrel 7247" available from DuPont-Toray Co., Ltd., tensile strength at 10% elongation: 24 MPa, surface hardness: 72D, melt volume rate: 14 cm³/10 min)

(A-15) Polyester elastomer having polybutylene naphthalate as structural units (the trade name "TQB-KET30" available from Teijin Limited, tensile strength at 10% elongation: 19 MPa, surface hardness: 64D, melt volume rate: 14 cm³/10 min)

(A-16) Styrene-based elastomer (the trade name "Septon 2104" available from Kuraray Co., Ltd., tensile strength at 10% elongation: 10 MPa, surface hardness: 55D, melt volume rate: 0.4 cm³/10 min)

(A-17) Acrylic-based elastomer (the trade name "Kurarity LM730H" available from Kuraray Co., Ltd., tensile strength at 10% elongation: 14 MPa, surface hardness: 64D, melt volume rate: 17 cm³/10 min)

Thermoplastic Resins Used in Comparative Examples (A-18) Polyester elastomer (the trade name "Hytrel 4047" available from DuPont-Toray Co., Ltd., tensile strength at 10% elongation: 8 MPa, surface hardness: 40D, melt volume rate: 8 cm³/10 min)

(A-19) Polyamide elastomer (the trade name "Pebax 3533" available from Arkema Inc., tensile strength at 10% elongation: 6 MPa, surface hardness: 33D, melt volume rate: 8 cm³/10 min)

(A-20) Olefin-based elastomer (the trade name "Prime TPO E-2910" available from Prime Polymer Co., Ltd., tensile strength at 10% elongation: 12 MPa, surface hardness: 64D, melt volume rate: 2.8 cm³/10 min)

(A-21) Polyacetal (the trade name "Duracon SX-35" available from Polyplastics Co., Ltd., tensile strength at 10% elongation: 22 MPa, surface hardness: 69D, melt volume rate: 5 cm³/10 min)

Hindered Amine Light Stabilizers (b)

(B-1) Tinuvin 622 SF (available from BASF, number average molecular weight: about 3,500, N—R type)

(B-2) Chimassorb 2020 FDL (available from BASF, number average molecular weight: about 3,000, N—H type)

(B-3) Chimassorb 944 FDL (available from BASF, number average molecular weight: about 2,300, N—H type)

(B-4) Sabostab UV 119 (available from Sabo S.p.A., number average molecular weight: 2,286, N—R type)

(B-5) Flamestab NOR 116 FF (available from BASF, number average molecular weight: 2,261, N—OR)

(B-6) ADK STAB LA-63P (available from Adeka Corporation, number average molecular weight: about 2,000, N—R type)

(B-7) ADK STAB LA-68 (available from Adeka Corporation, number average molecular weight: about 1,900, N—H type)

(B-8) ADK STAB LA-52 (available from Adeka Corporation, molecular weight: 847, N—R type)

(B-9) ADK STAB LA-57 (available from Adeka Corporation, molecular weight: 791, N—H type)

(B-10) Tinuvin 123 (available from BASF, molecular weight: 681, N—OR type)

(B-11) Tinuvin 765 (available from BASF, molecular weight: 509, N—R type) Hindered Amine Light Stabilizer Used in Comparative Examples (B-12) Tinuvin 770 DF (available from BASF, molecular weight: 481, N—H type)

Antioxidants (c)

(C-1) Sumilizer GP (available from Sumitomo Chemical Co., Ltd., phosphite-based)

(C-2) ADK STAB PEP-36A (available from Adeka Corporation, phosphite-based)

(C-3) ADK STAB AO-412S (available from Adeka Corporation, thioether-based)

(C-4) Irganox 1726 (available from BASF, thioether-based)

(C-5) Irganox 1330 (available from BASF, hindered phenol-based)

As can be seen from Table 1, Comparative Examples 1 to 6, which did not meet the requirements of the present invention, were unsatisfactory in terms of bending hardness, bending durability, or sterilization durability. As can be seen from the results for Comparative Example 5, the flexible tube for an endoscope that had a covering layer containing a polyolefin as a resin component was unsatisfactory in terms of bending durability even though it had a tensile strength at 10% elongation of 10 MPa or more. As can be seen from the results for Comparative Example 6, the flexible tube for an endoscope that had a covering layer containing a polyacetal as a resin component was unsatisfactory in terms of bending durability and sterilization durability even though it had a tensile strength at 10% elongation of 10 MPa or more.

In contrast, Examples 1 to 41, which met the requirements of the present invention, were satisfactory in all of the bending hardness, bending durability, and sterilization durability tests.

While the present invention has been described with reference to embodiments thereof, we do not intend to limit our invention in any detail of the description unless otherwise specified. Rather, the invention should be broadly construed without departing from the spirit and scope of the invention as defined by the appended claims.

REFERENCE SIGNS LIST 2 electronic endoscope (endoscope)
3 insertion section
   3a flexible tube
   3b angle portion
   3c tip portion
5 main-body operating section
6 universal cord
11 spiral tube
   11a metal strip
12 tubular net
13 cap
14 flexible tube substrate
15 resin layer

What is claimed is:

1. A flexible tube for an endoscope, comprising:
a flexible tube substrate that is flexible and tubular; and
a resin layer (A) covering the flexible tube substrate,
wherein the resin layer (A) includes a thermoplastic resin (a) including at least one of a polyamide resin, a polyurethane resin, a polyester resin, a polystyrene resin, or an acrylic resin and having a tensile strength at 10% elongation of 10 MPa or more and a hindered amine compound (b) having a molecular weight of 500 or more.

2. The flexible tube for an endoscope according to claim 1, wherein the thermoplastic resin (a) has a tensile strength at 10% elongation of 10 MPa to 50 MPa.

3. The flexible tube for an endoscope according to claim 1, wherein the polyamide resin includes at least one of polyamide 1010, polyamide 1012, polyamide 11, polyamide 12, a polyamide elastomer, or an amorphous polyamide.

4. The flexible tube for an endoscope according to claim 3, wherein the polyamide resin includes at least one of polyamide 11, polyamide 12, or a polyamide elastomer.

5. The flexible tube for an endoscope according to claim 1, wherein the polyurethane resin has an aliphatic diisocyanate-derived component.

6. The flexible tube for an endoscope according to claim 1, wherein the polyurethane resin has a poly(alkyleneoxy) structure in which the alkylene has 6 or more carbon atoms.

7. The flexible tube for an endoscope according to claim 1, wherein the polyester resin has a polybutylene naphthalate structure.

8. The flexible tube for an endoscope according to claim 1, wherein the acrylic resin has two or more acrylic acid ester components, each acrylic acid ester component forming a block structure.

9. The flexible tube for an endoscope according to claim 1, wherein the hindered amine compound (b) has a molecular weight of 1,000 or more.

10. The flexible tube for an endoscope according to claim 1, wherein the hindered amine compound (b) includes at least one of an N—R type hindered amine compound or an N—OR type hindered amine compound.

11. The flexible tube for an endoscope according to claim 1, wherein an amount of the hindered amine compound (b) is 0.2% to 8% by mass based on 100% by mass of all components forming the resin layer (A).

12. The flexible tube for an endoscope according to claim 1, wherein the resin layer (A) includes an antioxidant (c).

13. The flexible tube for an endoscope according to claim 12, wherein the antioxidant (c) includes at least one of a phosphite-based antioxidant or a thioether-based antioxidant.

14. The flexible tube for an endoscope according to claim 12, wherein an amount of the antioxidant (c) in the resin layer (A) is 0.15% to 4% by mass.

15. An endoscopic medical device comprising the flexible tube for an endoscope according to claim 1.

* * * * *